US009907493B2

United States Patent
Shiraishi

(10) Patent No.: US 9,907,493 B2
(45) Date of Patent: Mar. 6, 2018

(54) ENDOSCOPE SYSTEM PROCESSOR DEVICE, ENDOSCOPE SYSTEM, OPERATION METHOD FOR ENDOSCOPE SYSTEM PROCESSOR DEVICE, AND OPERATION METHOD FOR ENDOSCOPE SYSTEM

(71) Applicant: FUJIFILM Corporation, Tokyo (JP)

(72) Inventor: Yasushi Shiraishi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 528 days.

(21) Appl. No.: 14/574,529

(22) Filed: Dec. 18, 2014

(65) Prior Publication Data

US 2015/0201871 A1  Jul. 23, 2015

(30) Foreign Application Priority Data

Jan. 20, 2014  (JP) .................................. 2014-008166

(51) Int. Cl.
 A61B 5/1455  (2006.01)
 A61B 5/145  (2006.01)
 (Continued)

(52) U.S. Cl.
 CPC ...... *A61B 5/14542* (2013.01); *A61B 1/00009* (2013.01); *A61B 1/04* (2013.01);
 (Continued)

(58) Field of Classification Search
 None
 See application file for complete search history.

(56) References Cited

U.S. PATENT DOCUMENTS

2009/0270702 A1  10/2009  Zeng et al.
2011/0230715 A1   9/2011  Saito

FOREIGN PATENT DOCUMENTS

EP  2040218 A1   3/2009
EP  2505140 A1  10/2012
(Continued)

OTHER PUBLICATIONS

Notice of Reasons for Rejection for Japanese Application No. 2014-008166 dated Dec. 16, 2015, with English Translation.
(Continued)

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

There are provided an endoscope system processor device, an endoscope system, an operation method for an endoscope system processor device, and an operation method for an endoscope system for calculating objective diagnostic information, which is easier to understand than the oxygen saturation, based on the oxygen saturation. The endoscope system processor device includes: a receiving unit that receives an image signal obtained by imaging an observation target with an endoscope; an oxygen saturation calculation unit that calculates an oxygen saturation based on the image signal; a pixel specification unit that specifies an out-of-range pixel in which the oxygen saturation deviates from a specific range set in advance; and a diagnostic information calculation unit that calculates diagnostic information as a numerical value using information of the out-of-range pixel.

15 Claims, 18 Drawing Sheets

(51) Int. Cl.
*A61B 1/00* (2006.01)
*A61B 1/04* (2006.01)
*A61B 1/06* (2006.01)
*A61B 5/1459* (2006.01)
*G06T 7/00* (2017.01)

(52) U.S. Cl.
CPC ............... *A61B 1/043* (2013.01); *A61B 1/06* (2013.01); *A61B 1/063* (2013.01); *A61B 5/1459* (2013.01); *G06T 7/0012* (2013.01); *G06T 2207/10024* (2013.01); *G06T 2207/10068* (2013.01)

(56) References Cited

FOREIGN PATENT DOCUMENTS

| | | |
|---|---|---|
| JP | 6-319695 A | 11/1994 |
| JP | 2810718 B2 | 10/1998 |
| JP | 2011-194028 A | 10/2011 |
| JP | 2011-218135 A | 11/2011 |

OTHER PUBLICATIONS

Extended European Search Report for European Application No. 14198007.8, dated Jun. 16, 2015.

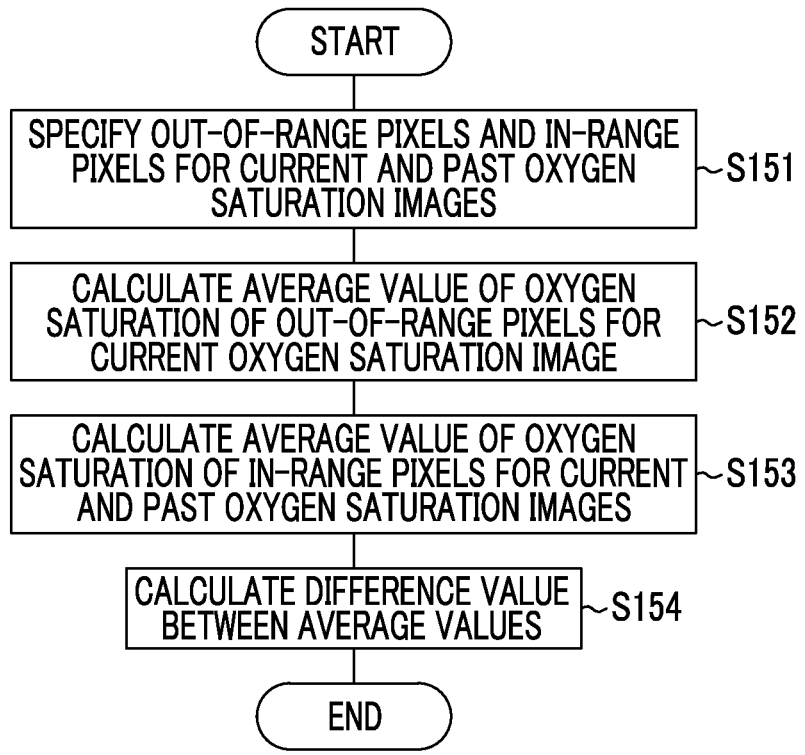
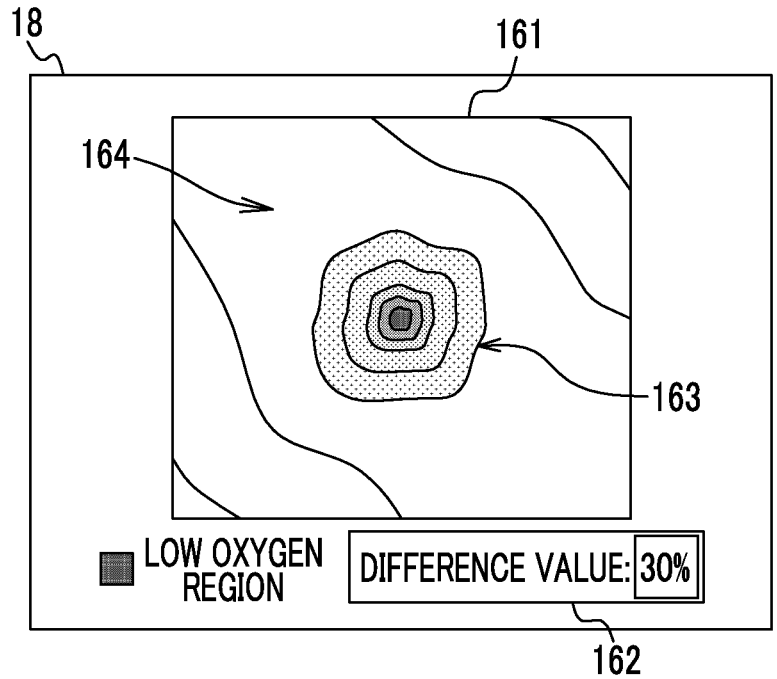

ENDOSCOPE SYSTEM PROCESSOR DEVICE, ENDOSCOPE SYSTEM, OPERATION METHOD FOR ENDOSCOPE SYSTEM PROCESSOR DEVICE, AND OPERATION METHOD FOR ENDOSCOPE SYSTEM

CROSS-REFERENCE TO RELATED APPLICATIONS

The present application claims priority under 35 U.S.C. § 119 to Japanese Patent Application No. 2014-008166, filed on Jan. 20, 2014, all of which are hereby expressly incorporated by reference into the present application.

BACKGROUND OF THE INVENTION

1. Field of the Invention

The present invention relates to an endoscope system processor device, an endoscope system, an operation method for an endoscope system processor device, and an operation method for an endoscope system for specifying biological function information regarding the oxygen saturation of blood hemoglobin from an image signal obtained by imaging an observation target in a subject.

2. Description of the Related Art

In the medical field, it is common to perform diagnosis using an endoscope system including a light source device, an endoscope, and a processor device. In recent years, diagnosis of a lesion using the oxygen saturation of blood hemoglobin in biological function information has been performed. As a method of acquiring the oxygen saturation, a method is known in which first signal light and second signal light having different waveguide bands and different light absorption coefficients for oxygenated hemoglobin and reduced hemoglobin are alternately emitted to blood vessels in the mucous membrane and reflected light beams of the first and second signal light beams are detected by a sensor located at the distal end of the endoscope (refer to JP2011-194028A).

The ratio between signal values (hereinafter, referred to as a signal ratio) of pixels of an image signal corresponding to the reflected light of the first signal light detected by the sensor and an image signal corresponding to the reflected light of the second signal light detected by the sensor is maintained as a fixed value if there is no change in the oxygen saturation in the blood vessel. However, if a change in the oxygen saturation occurs, the signal ratio changes with the oxygen saturation change. Accordingly, it is possible to calculate the oxygen saturation based on the signal ratio of the image signals.

As a display method of the oxygen saturation, a method of performing pseudo-color display of a difference value with respect to the oxygen saturation in a reference region set in advance is known (refer to JP2011-194028A and JP1994-319695A (JP-H06-319695A)). There is also an example of performing numerical display of the calculated oxygen saturation (refer to JP2810718B).

SUMMARY OF THE INVENTION

Although the oxygen saturation is a useful indicator for diagnosis, the oxygen saturation may not always be a straightforward indicator that is directly related to the diagnosis. For example, in lesions, such as cancer, the oxygen saturation is generally low. Therefore, if pseudo-color display of a location of low oxygen saturation is displayed based on the oxygen saturation as disclosed in JP2011-194028A and JP1994-319695A (JP-H06-319695A), it is possible to indicate the location of a suspected lesion. However, although the oxygen saturation of normal tissue or lesions, such as cancer, generally falls within a fixed range, the range is relatively wide, and there is a variation depending on the subject. For this reason, when performing pseudo-color display according to uniform criteria that do not depend on the subject, in order to diagnose whether a location in pseudo-color display is a lesion or normal tissue according to individual differences in the subject, skill may be required in the doctor. For example, it is necessary to observe the differences in color with respect to normal tissue and the like in detail. The same is true for the case of performing numerical display of the oxygen saturation as disclosed in JP2810718B.

For this reason, it is preferable that an endoscope system that calculates the oxygen saturation not only simply calculate and display the oxygen saturation but also present the calculated oxygen saturation as objective information (hereinafter, referred to as diagnostic information) that is easier to understand and is directly related to the diagnosis. It is an object of the invention to provide an endoscope system processor device, an endoscope system, an operation method for an endoscope system processor device, and an operation method for an endoscope system for specifying objective diagnostic information, which is easier to understand than the oxygen saturation, based on the oxygen saturation.

An endoscope system processor device of the invention includes: a receiving unit that receives an image signal obtained by imaging an observation target with an endoscope; an oxygen saturation calculation unit that calculates an oxygen saturation based on the image signal; a pixel specification unit that specifies an out-of-range pixel in which the oxygen saturation deviates from a specific range set in advance; and a diagnostic information calculation unit that calculates diagnostic information as a numerical value using information of the out-of-range pixel.

For example, the pixel specification unit also specifies an in-range pixel in which the oxygen saturation is within the specific range set in advance, and the diagnostic information calculation unit includes a difference value calculation section that calculates a difference value between the oxygen saturation of the out-of-range pixel and the oxygen saturation of the in-range pixel.

In this case, the difference value calculation section includes a first average value calculation section that calculates an average value of the oxygen saturation of the out-of-range pixels and a second average value calculation section that calculates an average value of the oxygen saturation of the in-range pixels, and calculates a difference value between a first average value calculated by the first average value calculation section and a second average value calculated by the second average value calculation section.

More specifically, the first average value calculation section calculates the first average value using one oxygen saturation, and the second average value calculation section calculates the second average value using a plurality of oxygen saturations.

In particular, it is preferable that the first average value calculation section calculate the first average value using the current oxygen saturation and the second average value calculation section calculate the second average value using the current and past oxygen saturations.

In addition, the first average value calculation section may calculate the first average value using one specific oxygen saturation of the plurality of past oxygen saturations, and the second average value calculation section may calculate the second average value using the plurality of past oxygen saturations.

The diagnostic information calculation unit may include a measurement section that measures a size of a region formed by the out-of-range pixels.

The diagnostic information calculation unit may include an occupancy calculation section that calculates an occupancy indicating a proportion of the out-of-range pixels in a set region of interest.

The diagnostic information calculation unit may include a statistic calculation section that calculates a statistic regarding distribution of the out-of-range pixels in the set region of interest.

An endoscope system of the invention includes: a light source that emits light for irradiating an observation target; an imaging device that images the observation target and outputs an image signal; an oxygen saturation calculation unit that calculates an oxygen saturation based on the image signal; a pixel specification unit that specifies an out-of-range pixel in which the oxygen saturation deviates from a specific range; and a diagnostic information calculation unit that calculates diagnostic information as a numerical value using information of the out-of-range pixel.

An operation method for an endoscope system processor device of the invention includes: a receiving step in which a receiving unit receives an image signal obtained by imaging an observation target with an endoscope; an oxygen saturation calculation step in which an oxygen saturation calculation unit calculates an oxygen saturation based on the image signal; a pixel specification step in which a pixel specification unit specifies an out-of-range pixel in which the oxygen saturation deviates from a specific range set in advance; and a diagnostic information calculation step in which a diagnostic information calculation unit calculates diagnostic information as a numerical value using information of the out-of-range pixel.

An operation method for an endoscope system of the invention includes: an imaging step in which an imaging device images an observation target with light emitted from a light source to the observation target and outputs an image signal; an oxygen saturation calculation step in which an oxygen saturation calculation unit calculates an oxygen saturation based on the image signal; a pixel specification step in which a pixel specification unit specifies an out-of-range pixel in which the oxygen saturation deviates from a specific range set in advance; and a diagnostic information calculation step in which a diagnostic information calculation unit calculates diagnostic information as a numerical value using information of the out-of-range pixel.

According to the endoscope system processor device, the endoscope system, the operation method for an endoscope system processor device, and the operation method for an endoscope system of the invention, it is possible to acquire objective diagnostic information, that is easier to understand than the oxygen saturation, based on the oxygen saturation and to provide the objective diagnostic information to a doctor.

BRIEF DESCRIPTION OF THE DRAWINGS

FIG. 13 is a flowchart showing a method of calculating diagnostic information.
FIG. 14 is an explanatory diagram showing the operation in a first embodiment.

DESCRIPTION OF THE PREFERRED EMBODIMENTS

Figure 1:
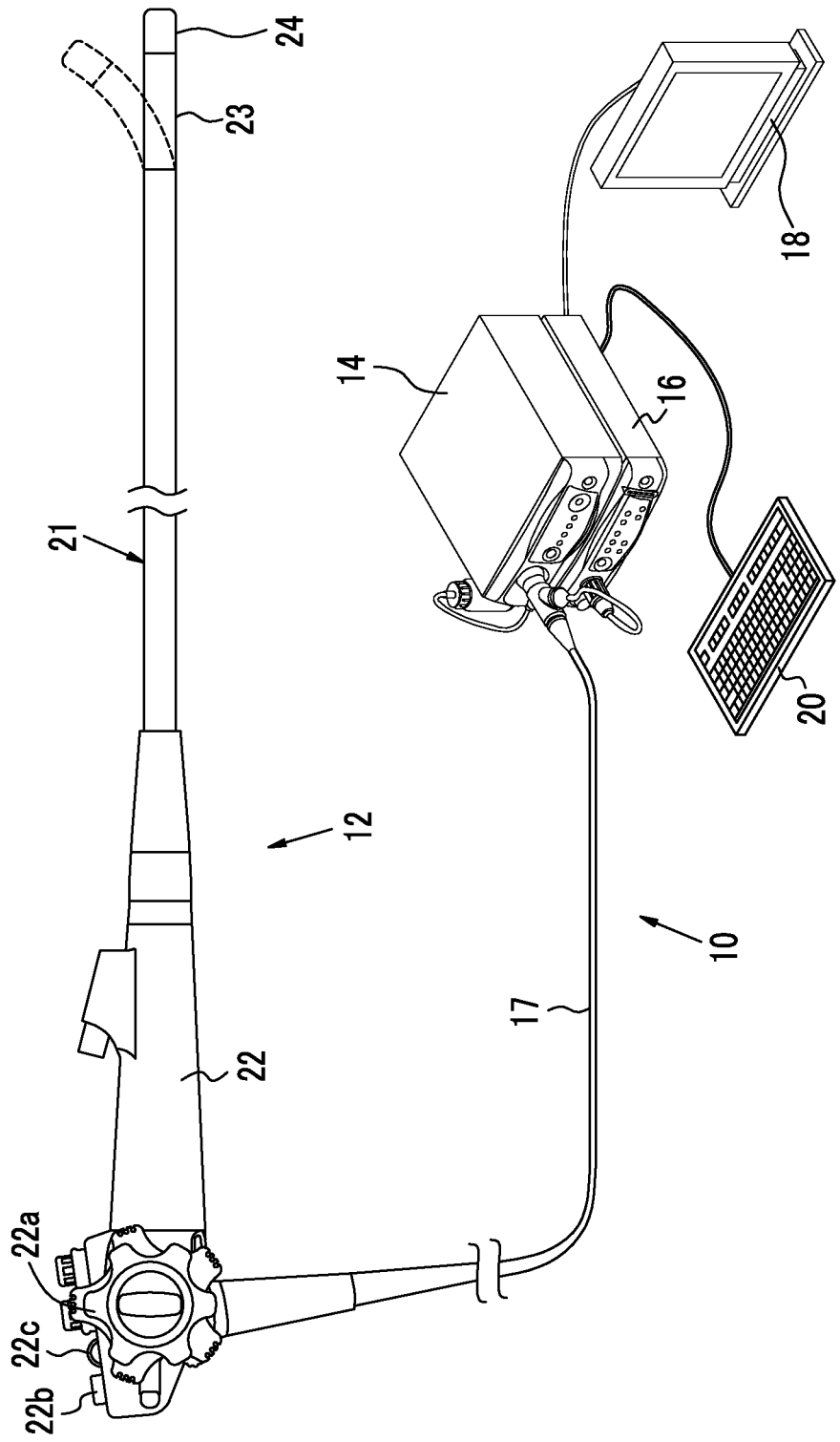
FIG. 1 is an external view of an endoscope system.

[First Embodiment]
As shown in FIG. 1, an endoscope system 10 according to a first embodiment includes an endoscope 12, a light source device 14, a processor device 16, a monitor 18 (display unit), and a console 20. The endoscope 12 is optically connected to the light source device 14, and is electrically connected to the processor device 16. The endoscope 12 includes an inserted portion 21 that is inserted into a subject, an operating portion 22 provided at the base end of the inserted portion 21, and a bending portion 23 and a distal portion 24 that are provided at the distal side of the inserted portion 21. By operating an angle knob 22a of the operating portion 22, the bending portion 23 is bent. The distal portion 24 can be directed in a desired direction by the bending operation.

In addition to the angle knob 22a, an observation mode selector SW (observation mode selector switch) 22b, a zoom operation portion 22c, and a freeze button (not shown) for saving a still image are provided in the operating portion 22. The mode selector SW 22b is used for a switching operation between two modes of the normal observation mode and the special observation mode. The normal observation mode is a mode in which a normal light image obtained by full-color imaging of the observation target in the subject is displayed on the monitor 18. The special observation mode is a mode in which an oxygen saturation image obtained by imaging of the oxygen saturation of blood hemoglobin of the observation target is displayed on the monitor 18. The zoom operation portion 22c is used for a zooming operation for driving a zoom lens 47 (refer to FIG. 2) in the endoscope 12 to magnify the observation target.

The processor device 16 is electrically connected to the monitor 18 and the console 20. The monitor 18 displays an image, such as a normal light image or an oxygen saturation image, and information regarding the image (hereinafter, referred to as image information or the like). The console 20 functions as a user interface (UI) for receiving an input operation, such as a function setting. In addition, a recording unit (not shown) in which image information or the like is recorded may be connected to the processor device 16.

Figure 2:
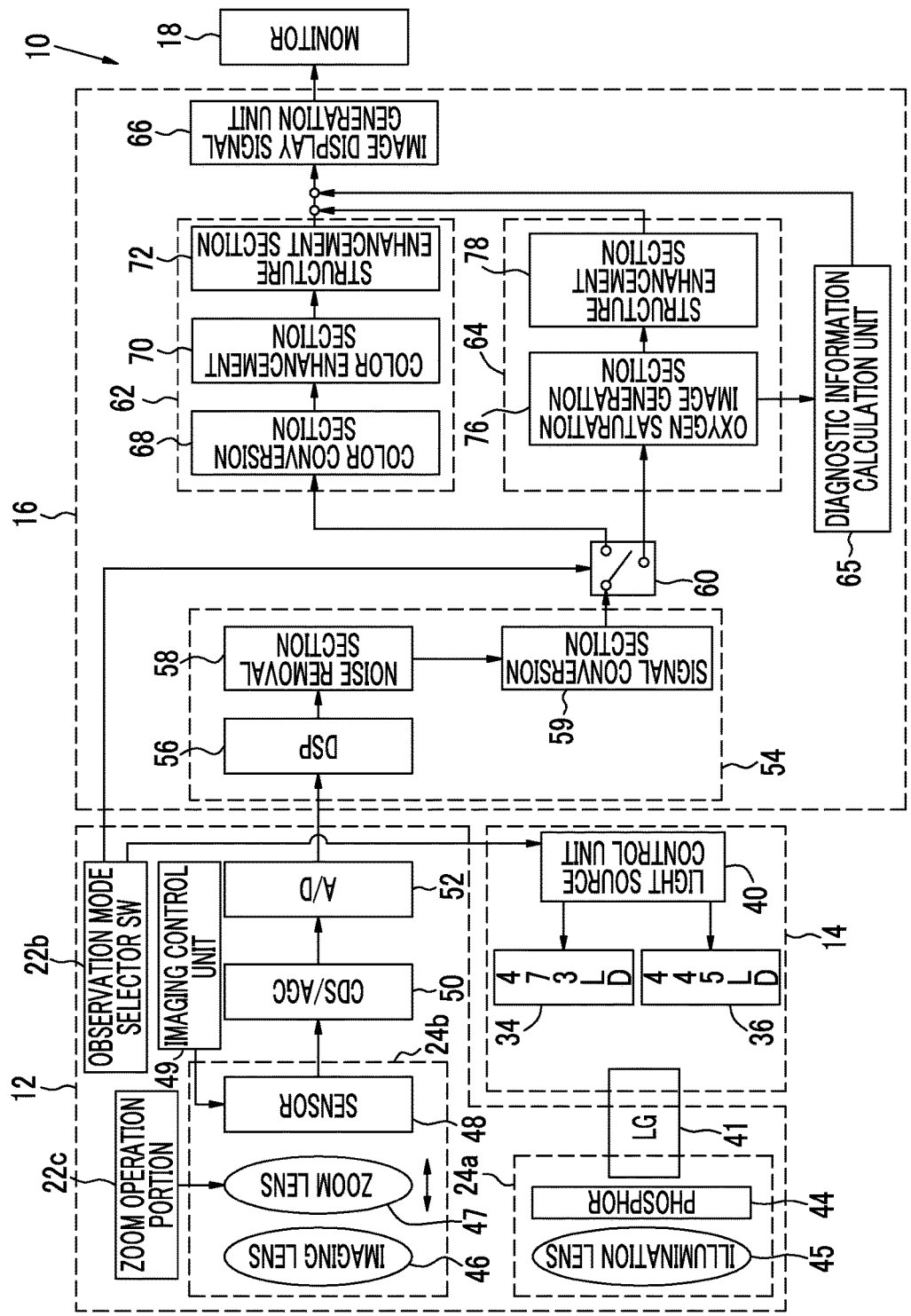
FIG. 2 is a block diagram of the endoscope system.

As shown in FIG. 2, the light source device 14 includes, as light emitting sources, a first blue laser light source (473 LD (laser diode)) 34 that emits first blue laser light having a center wavelength of 473 nm and a second blue laser light source (445 LD) 36 that emits second blue laser light having a center wavelength of 445 nm. The light emission amount and the light emission timing of each of the light sources 34 and 36 formed of the semiconductor light emitting elements are separately controlled by a light source control unit 40. For this reason, the light intensity ratio between light emitted from the first blue laser light source 34 and light emitted from the second blue laser light source 36 can be freely changed. In addition, it is preferable that the half-width of each of the first and second blue laser light beams be set to about ±10 nm. As the first blue laser light source 34 and the second blue laser light source 36, a broad area type InGaN-based laser diode can be used, or an InGaNAs-based laser diode or a GaNAs-based laser diode can be used. In addition, as the light sources, it is possible to use a structure using a light emitter, such as a light emitting diode.

The light source control unit 40 turns on the second blue laser light source 36 in the normal observation mode. On the other hand, in the special observation mode, the light source control unit 40 turns on the first blue laser light source 34 and the second blue laser light source 36 alternately at intervals of one frame.

The first and second blue laser light beams emitted from the light sources 34 and 36 are incident on a light guide (LG) 41 through optical members, such as a condensing lens, an optical fiber, and a multiplexer (none is shown). The light guide 41 is built into a universal cord 17 that connects the endoscope 12 and the light source device 14 to each other (refer to FIG. 1) and the endoscope 12. The light guide 41 causes the first and second blue laser light beams to propagate from the light sources 34 and 36 to the distal portion 24 of the endoscope 12 therethrough. As the light guide 41, a multi-mode fiber can be used. As an example, it is possible to use a small-diameter fiber cable having a diameter of φ0.3 mm to φ0.5 mm that includes a core with a diameter of 105 μm, a cladding with a diameter of 125 μm, and a protective layer as an outer skin.

The distal portion 24 of the endoscope 12 includes an illumination optical system 24a and an imaging optical system 24b. A phosphor 44 and an illumination lens 45 are provided in the illumination optical system 24a. The first and second blue laser light beams are incident on the phosphor 44 from the light guide 41. The phosphor 44 emits fluorescence due to the first or second blue laser light emitted thereto. Some of the first or second blue laser light beams are transmitted through the phosphor 44. The light emitted from the phosphor 44 is emitted to the observation target through the illumination lens 45. The first blue laser light source 34, the second blue laser light source 36, and the phosphor 44 form a light source that emits illumination light to the observation target.

Figure 3:
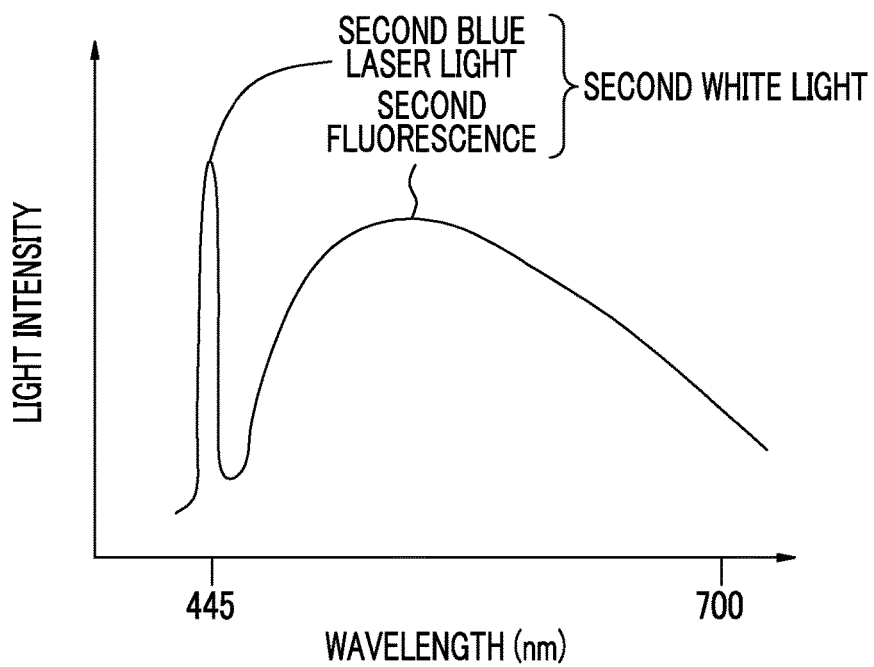
FIG. 3 is a graph showing the spectrum of light emitted in a normal observation mode.

In the normal observation mode, the second blue laser light is incident on the phosphor 44. Accordingly, white light having a spectrum shown in FIG. 3 (hereinafter, referred to as second white light) is emitted to the observation target as illumination light. The second white light is configured to include second blue laser light and second fluorescence of green to red that is excited and emitted from the phosphor 44 by the second blue laser light. Accordingly, the wavelength range of the second white light is the entire visible light region.

Figure 4:
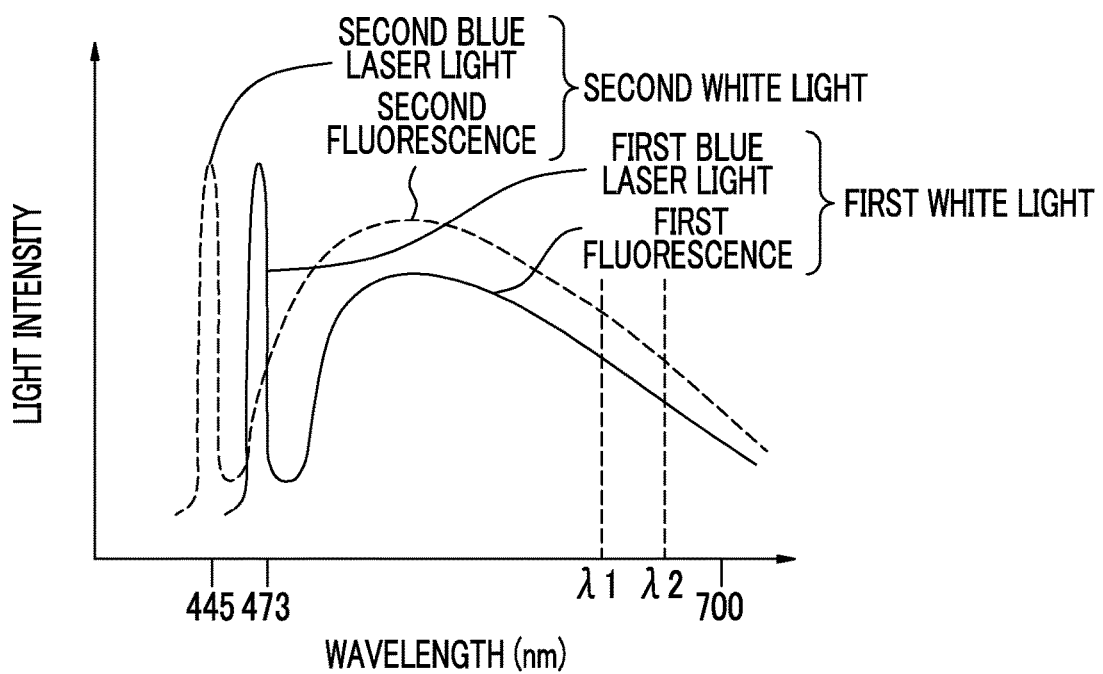
FIG. 4 is a graph showing the spectrum of light emitted in a special observation mode.

On the other hand, in the special observation mode, the first blue laser light and the second blue laser light are alternately incident on the phosphor 44. Therefore, as shown in FIG. 4, first white light and second white light having different emission spectrums are alternately emitted to the observation target as illumination light. The first white light is configured to include first blue laser light and first fluorescence of green to red that is excited and emitted from the phosphor 44 by the first blue laser light. Accordingly, the wavelength range of the first white light is the entire visible light region. The second white light is the same as the second white light emitted in the normal observation mode. In the present embodiment, the first white light is first illumination light, and the second white light is second illumination light.

The first fluorescence and the second fluorescence have almost the same waveform (shape of the spectrum), and the ratio between the intensity ($I1 (\lambda)$) of the first fluorescence and the intensity ($I2 (\lambda)$) of the second fluorescence (hereinafter, referred to as an inter-frame intensity ratio) is the same at any wavelength $\lambda$. For example, it is $I2 (\lambda 1)/I1 (\lambda 1)=I2 (\lambda 2)/I1 (\lambda 2)$. Since the inter-frame intensity ratio $I2 (\lambda)/I1 (\lambda)$ affects the calculation accuracy of the oxygen saturation, the inter-frame intensity ratio $I2 (\lambda)/I1 (\lambda)$ is accurately controlled by the light source control unit 40 such that the intensity ratio between reference frames set in advance is maintained.

As the phosphor 44, it is preferable to use a phosphor that absorbs some of the first and second blue laser light beams and includes a plurality of kinds of phosphor (for example, a YAG-based phosphor or a phosphor, such as BAM ($BaMgAl_{10}O_{17}$)) that are excited to emit green to red light beams. If a semiconductor light emitting element is used as a light source for exciting the phosphor 44 as in the present embodiment, it is possible to obtain high-intensity first and second white light beams having high luminous efficiency. In addition, it is possible to easily adjust the intensity of the white light and to suppress changes in color temperature and chromaticity.

The imaging optical system 24b of the endoscope 12 includes an imaging lens 46, the zoom lens 47, and a sensor

48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation portion 22c. When the zoom lens 47 is moved to the tele end side, the reflected image of the observation target is magnified. On the other hand, when the zoom lens 47 is moved to the wide end side, the reflected image of the observation target is reduced. In addition, when magnified observation is not performed (at the time of non-magnified observation), the zoom lens 47 is disposed at the wide end. When performing magnified observation, the zoom lens 47 is moved from the wide end to the tele end side by operating the zoom operation portion 22c.

The sensor 48 is a color imaging device, and captures a reflected image of the observation target and outputs the image signal. As the sensor 48, for example, a charge coupled device (CCD) image sensor or a complementary metal oxide semiconductor (CMOS) image sensor can be used. In the present embodiment, the sensor 48 is a CCD image sensor. In addition, the sensor 48 includes RGB pixels in which RGB color filters are provided on the imaging surface, and outputs image signals of three colors of R, G, and B by performing photoelectric conversion with the pixels of respective colors of RGB.

Figure 5:
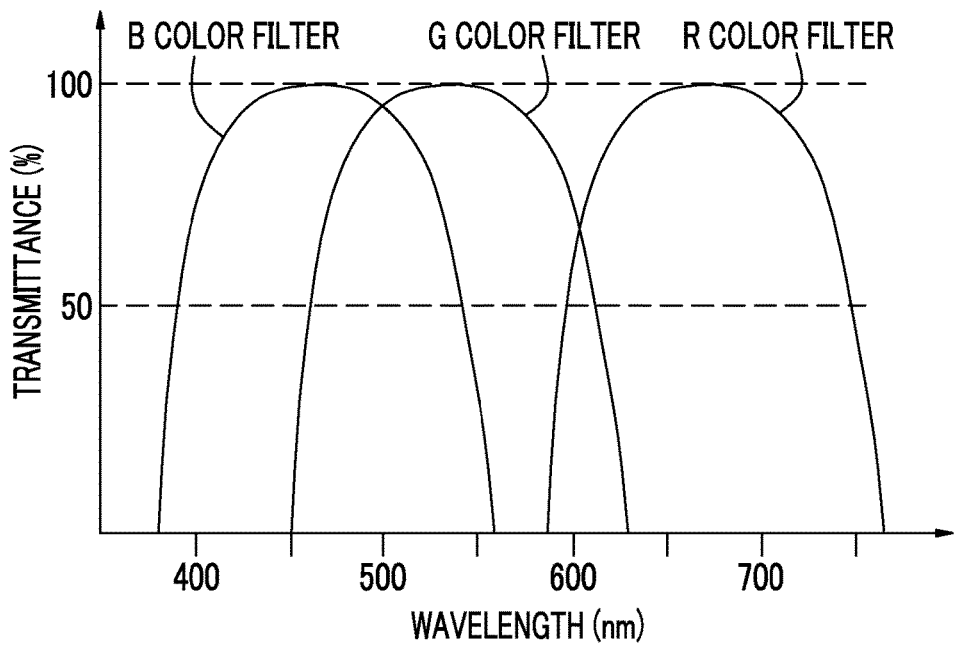
FIG. 5 is a graph showing the spectral transmittance of an RGB color filter.

As shown in FIG. 5, the B color filter has a spectral transmittance of 380 nm to 560 nm, the G color filter has a spectral transmittance of 450 nm to 630 nm, and the R color filter has a spectral transmittance of 580 nm to 760 nm. Accordingly, when the second white light is emitted to the observation target in the normal observation mode, the second blue laser light and some of green components of the second fluorescence are incident on the B pixel, some of green components of the second fluorescence are incident on the G pixel, and red components of the second fluorescence are incident on the R pixel. In the B image signal output from the B pixel, the emission intensity of the second blue laser light is extremely larger than that of the second fluorescence. Accordingly, most of the B image signal is occupied by the reflected light components of the second blue laser light.

On the other hand, when the first white light is emitted to the observation target in the special observation mode, the first blue laser light and some of green components of the first fluorescence are incident on the B pixel, some of green components of the first fluorescence and the first blue laser light attenuated by the G color filter are incident on the G pixel, and red components of the first fluorescence are incident on the R pixel. Since the emission intensity of the first blue laser light is extremely larger than that of the first fluorescence, most of the B image signal output from the B pixel is occupied by the reflected light components of the first blue laser light.

Light incidence components in the respective RGB pixels when the second white light is emitted to the observation target in the special observation mode are the same as those in the normal observation mode.

As the sensor 48, it is also possible to use a so-called complementary color image sensor including complementary color filters of C (cyan), M (magenta), Y (yellow), and G (green) on the imaging surface. When using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even when complementary color image sensors are used, it is possible to obtain the image signals of three colors of RGB from the image signals of four colors of CMYG by color conversion.

Figure 6:
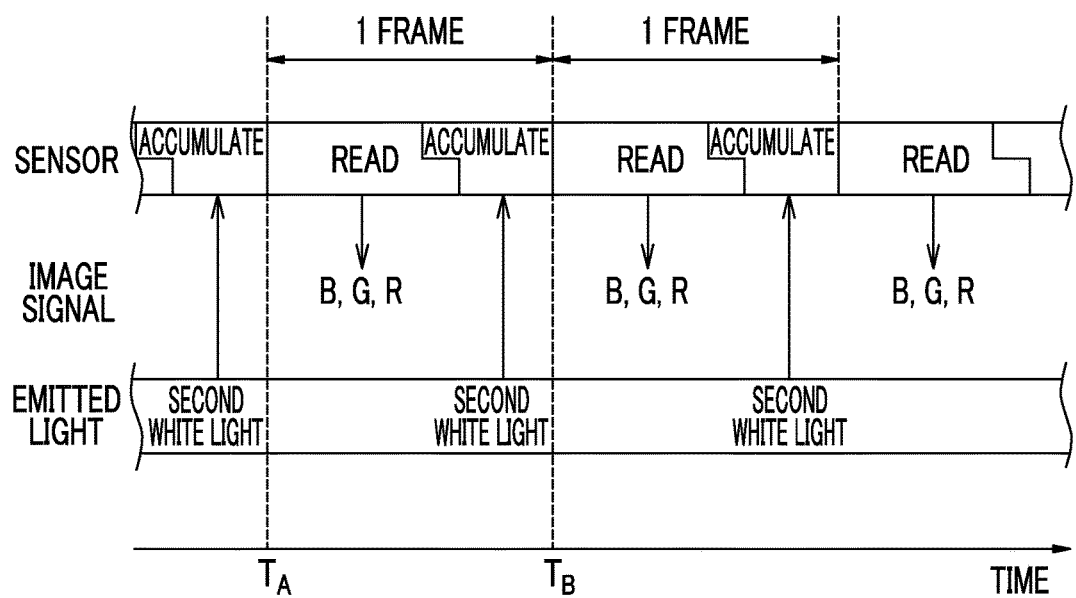
FIG. 6 is an explanatory diagram showing imaging control in the normal observation mode.

An imaging control unit 49 performs imaging control of the sensor 48. As shown in FIG. 6, in the normal observation mode, an observation target illuminated by the second white light is imaged by the sensor 48 every period of one frame (hereinafter, simply referred to as one frame). Then, the image signals of RGB are output from the sensor 48 for each frame. In the present embodiment, the sensor 48 is a CCD image sensor. Accordingly, one frame is a period of the length from the end (time $T_A$) of a charge accumulation period (also referred to as an exposure period) to the end of the next charge accumulation period (time $T_B$), for example. In addition, since the sensor 48 is a CCD image sensor, one frame is divided into a reading period and a charge accumulation period in FIG. 6. However, the approximately entire one frame can be set as a charge accumulation period, and signal charges accumulated in the previous frame can also be read during the accumulation of signal charges. The imaging control unit 49 also performs control, such as the adjustment of the length of the charge accumulation period.

Figure 7:
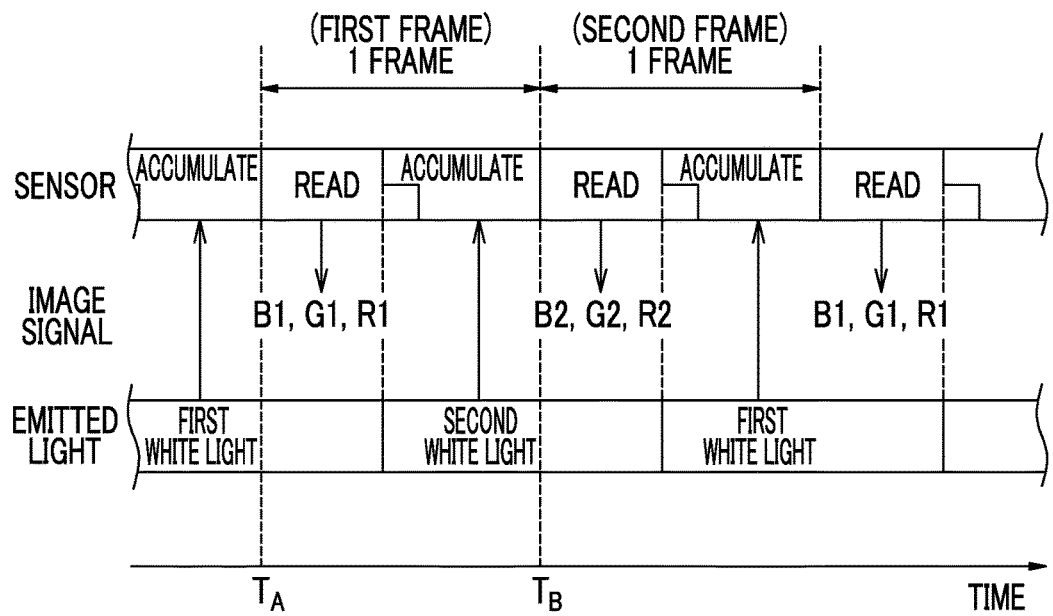
FIG. 7 is an explanatory diagram showing imaging control in the special observation mode.

Also in the special observation mode, the imaging control unit 49 performs imaging control of the sensor 48 in the same manner as in the normal observation mode. However, in the special observation mode, the first white light and the second white light are alternately emitted to the observation target in synchronization with the imaging frame of the sensor 48. Therefore, as shown in FIG. 7, the sensor 48 reads signal charges, which are obtained by imaging the observation target under the first white light, to the reading period of the first frame, and outputs the image signals of RGB colors. Then, the sensor 48 reads signal charges, which are obtained by imaging the observation target under the second white light, to the reading period of the second frame, and outputs the image signals of RGB colors. The sensor 48 outputs the image signals of RGB colors in both the first and second frames. However, the spectrum of white light in the first frame and the spectrum of white light in the second frame are different. Therefore, for the sake of distinction, the image signals of RGB colors that the sensor 48 outputs in the first frame are referred to as an R1 image signal, a G1 image signal, and a B1 image signal, and the image signals of RGB colors that the sensor 48 outputs in the second frame are referred to as an R2 image signal, a G2 image signal, and a B2 image signal.

In addition, in order to calculate the oxygen saturation, for example, a signal ratio B1/G2 between the B1 image signal and the G2 image signal and a signal ratio R2/G2 between the R2 image signal and the G2 image signal are used. Between these signal ratios, the signal ratio B1/G2 between the B1 image signal and the G2 image signal is a signal ratio that is required for the calculation of the oxygen saturation. For this reason, a component (first blue laser light transmitted through the phosphor 44) that becomes the B1 image signal in the first white light is the first signal light, and a component (green band component of the second fluorescence) that becomes the G2 image signal in the second white light is the second signal light.

The image signals of the respective colors output from the sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes a receiving unit 54, an image processing switching unit 60, a normal observation image processing unit 62, a special observation image processing unit 64, a diagnostic information calculation unit 65, and an image display signal generation unit 66. The receiving unit 54 receives the image signal input from the endoscope 12. The receiving unit 54 includes a digital signal processor (DSP) 56, a noise removal section 58, and a signal conversion section 59.

The DSP 56 performs various kinds of signal processing, such as defect correction processing, offset processing, gain correction processing, linear matrix processing, gamma conversion processing, demosaic processing, and YC conversion processing, on the received image signal. In the defect correction processing, the signal of the defective pixel of the sensor 48 is corrected. In the offset processing, a dark current component is removed from the image signal subjected to the defect correction processing, and the exact zero level is set. In the gain correction processing, the signal level of each image signal is adjusted by multiplying each of the RGB image signals after the offset processing by a specific gain. Linear matrix processing for increasing color reproducibility is performed on the image signal of each color after the gain correction processing. Then, the brightness or saturation of each image signal is adjusted by gamma conversion processing. Demosaic processing (also referred to as isotropic processing or synchronization processing) is performed on the image signal after the linear matrix processing, and the signal of missing color of each pixel is generated by interpolation. Through the demosaic processing, all pixels have signals of RGB colors. The signal conversion section 59 performs YC conversion processing on each image signal after the demosaic processing, and outputs a brightness signal Y and color difference signals Cb and Cr to the noise removal section 58.

The noise removal section 58 performs noise removal processing using, for example, a moving average method or a median filter method on the image signal subjected to the demosaic processing or the like by the DSP 56. The image signals after noise has been removed are input to the signal conversion section 59, are reconverted into RGB image signals, and are input to the image processing switching unit 60.

When the observation mode selector SW22b is set to the normal observation mode, the image processing switching unit 60 inputs the image signals to the normal observation image processing unit 62. On the other hand, when the observation mode selector SW22b is set to the special observation mode, the image processing switching unit 60 inputs the image signals to the special observation image processing unit 64.

The normal observation image processing unit 62 includes a color conversion section 68, a color enhancement section 70, and a structure enhancement section 72. The color conversion section 68 generates RGB image data by assigning the input RGB image signals of one frame to R, G, and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the image display signal generation unit 66 as a normal observation image.

The special observation image processing unit 64 includes an oxygen saturation image generation section 76 and a structure enhancement section 78. The oxygen saturation image generation section 76 calculates the oxygen saturation, and generates an oxygen saturation image indicating the calculated oxygen saturation.

The structure enhancement section 78 performs structure enhancement processing, such as spatial frequency enhancement processing, on the oxygen saturation image input from the oxygen saturation image generation section 76. The oxygen saturation image subjected to the structure enhancement processing by the structure enhancement section 72 is input to the image display signal generation unit 66.

The diagnostic information calculation unit 65 acquires the oxygen saturation that is calculated in the process of generating the oxygen saturation image by the oxygen saturation image generation section 76. Then, using the oxygen saturation, diagnostic information that is easier to understand than the oxygen saturation and is directly related to the diagnosis is calculated as a numerical value. In the present embodiment, the diagnostic information calculation unit 65 calculates, as diagnostic information, a difference value of the oxygen saturation of a region of low oxygen saturation indicating a diseased tissue (hereinafter, referred to as a low oxygen region) with respect to the oxygen saturation of a region of high oxygen saturation indicating a normal tissue (hereinafter, referred to as a high oxygen region). The difference value indicates the lowness of the oxygen saturation of the low oxygen region with respect to the oxygen saturation of the high oxygen region that changes with a subject. That is, since the difference value is a numerical value that does not depend on individual differences, the difference value is an indicator of diagnosis that is more objective and is easier to understand than the oxygen saturation.

The image display signal generation unit 66 converts the normal observation image or the oxygen saturation image into a display format signal (display image signal), and inputs the display format signal to the monitor 18. As a result, the normal observation image or the oxygen saturation image is displayed on the monitor 18. In addition, in the special observation mode, the diagnostic information is input to the image display signal generation unit 66 from the diagnostic information calculation unit 65. Accordingly, the image display signal generation unit 66 displays the oxygen saturation image and the diagnostic information on the monitor 18.

Figure 8:
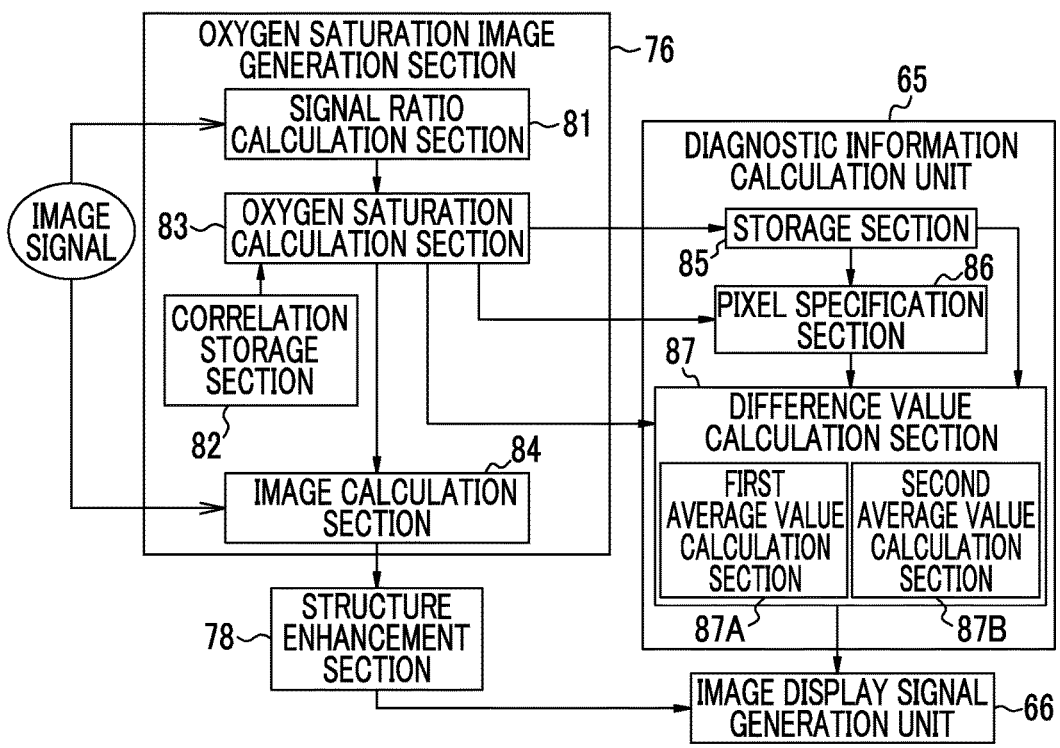
FIG. 8 is a block diagram of an oxygen saturation image generation section and a diagnostic information calculation unit.

As shown in FIG. 8, the oxygen saturation image generation section 76 includes a signal ratio calculation section 81, a correlation storage section 82, an oxygen saturation calculation section 83, and an image generation section 84.

The signal ratio calculation section 81 calculates a signal ratio that is used when the oxygen saturation calculation section 83 calculates the oxygen saturation. Specifically, the signal ratio calculation section 81 calculates the signal ratio B1/G2 between the B1 image signal and the G2 image signal for each pixel, and calculates the signal ratio R2/G2 between the R2 image signal and the G2 image signal for each pixel. When calculating the signal ratio B1/G2, the signal ratio calculation section 81 uses the B1 image signal that is corrected to the signal value based on almost only the first blue laser light by performing correction processing for enhancing the color separability by removing the signal value based on the first fluorescence from the B1 image signal by inter-pixel calculation using the B1 image signal, the G1 image signal, and the R1 image signal.

Figure 9:
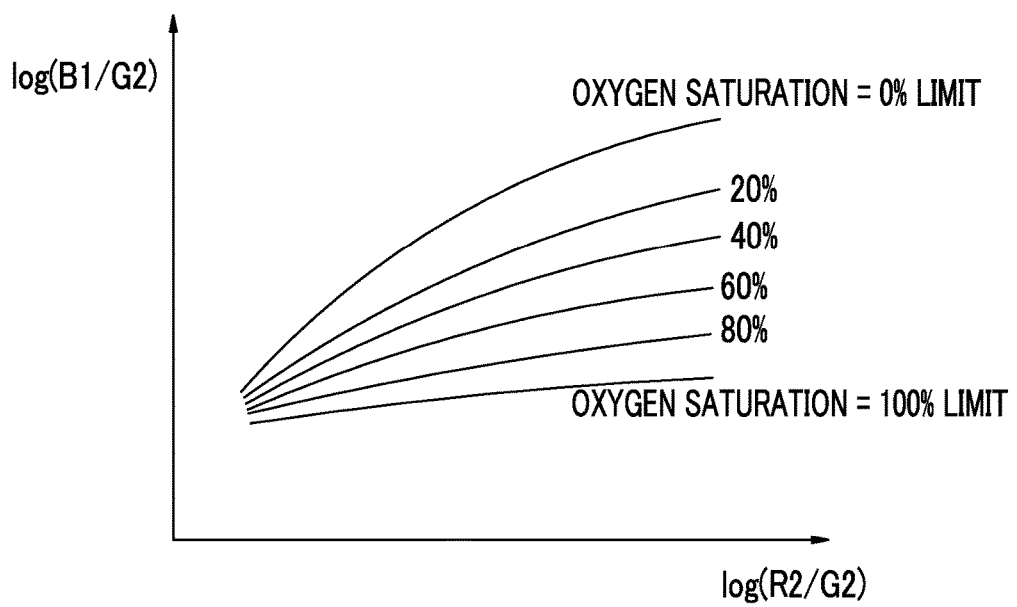
FIG. 9 is a graph showing the correlation between the signal ratio and the oxygen saturation.

The correlation storage section 82 stores a correlation between the signal ratio calculated by the signal ratio calculation section 81 and the oxygen saturation. This correlation is stored in a two-dimensional table that defines the isolines of the oxygen saturation on a two-dimensional space shown in FIG. 9. In the present embodiment, the correlation is used commonly in first and second calculation modes. The position and shape of the isolines for the signal ratio are obtained in advance by physical simulation of light scattering, and the distance between isolines changes according to the blood volume (horizontal axis in FIG. 9). In addition, the correlation between the signal ratio and the oxygen saturation is stored in a log scale.

Figure 10:
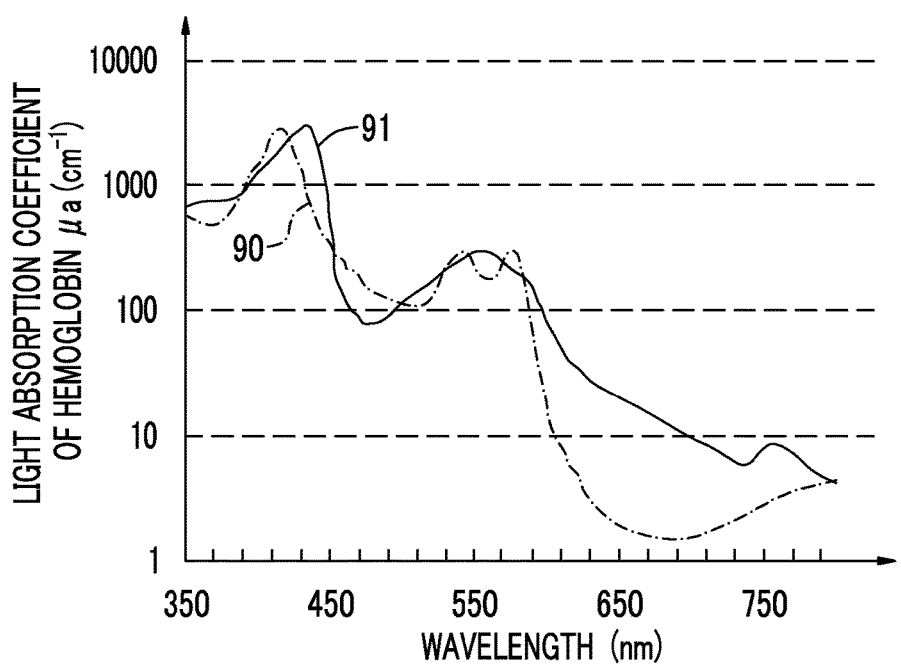
FIG. 10 is a graph showing the light absorption coefficients of oxygenated hemoglobin and reduced hemoglobin.

As shown in FIG. 10, this correlation is closely related to the absorption characteristics or light scattering characteristics of oxygenated hemoglobin (graph 90) or reduced hemoglobin (graph 91). For example, as at a center wavelength of 473 nm of the first blue laser light, at a wavelength at which the difference between the light absorption coefficient of oxygenated hemoglobin and the light absorption coefficient of reduced hemoglobin is large, it is easy to handle the information of the oxygen saturation. However, the B1 image signal including a signal corresponding to 473-nm light has a high dependence not only on the oxygen saturation but also on the blood volume. Therefore, by using the signal ratio R2/G2 obtained from the R2 image signal and the G2 image signal as well as the B1 image signal, it is possible to accurately calculate the oxygen saturation without there being dependency on the blood volume. Here, the R2 image signal corresponds to light that changes mainly depending on the blood volume, and the G2 image signal is a reference signal of the B1 image signal and the R2 image signal.

Figure 11:
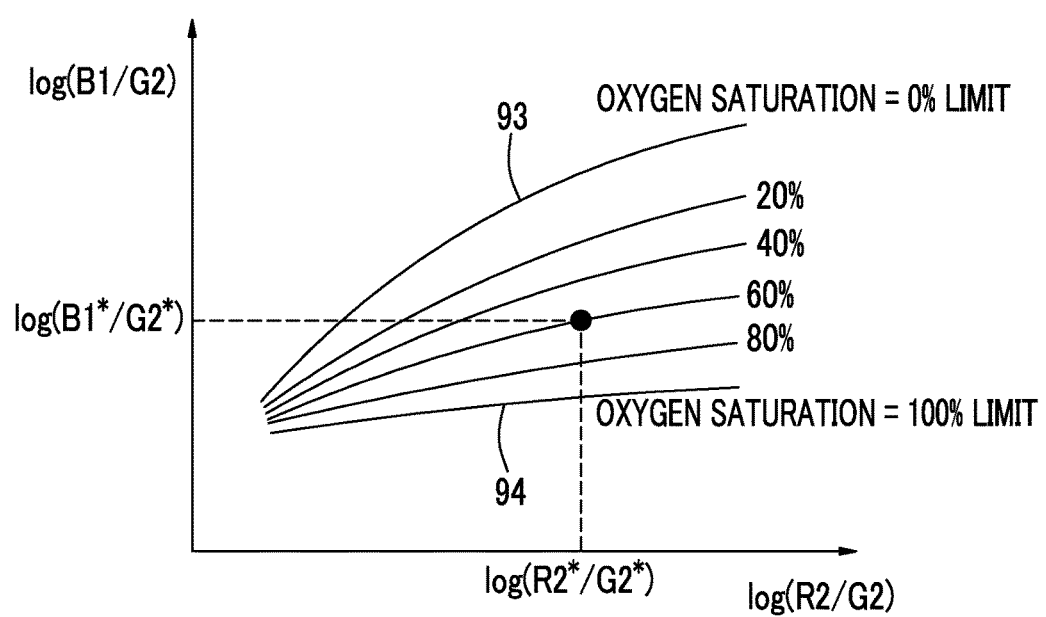
FIG. 11 is an explanatory diagram showing a method of calculating the oxygen saturation.

By using the signal ratio calculated by the signal ratio calculation section 81, the oxygen saturation calculation section 83 calculates the oxygen saturation based on the amount of movement. More specifically, the oxygen saturation calculation section 83 calculates the oxygen saturation corresponding to the signal ratio calculated by the signal ratio calculation section 81, for each pixel, with reference to the correlation stored in the correlation storage section 82. For example, when the signal ratio B1/G2 and the signal ratio R2/G2 in a specific pixel are B1*/G2* and R2*/G2*, respectively, the oxygen saturation corresponding to the signal ratio B1*/G2* and the signal ratio R2*/G2* is "60%" when the correlation shown in FIG. 11 is referred to. Accordingly, the oxygen saturation calculation section 83 calculates the oxygen saturation of the specified pixel as "60%".

In addition, a case where the signal ratio B1/G2 and the signal ratio R2/G2 becomes extremely large or extremely small hardly occurs. That is, a case hardly occurs in which the value of the signal ratio B1/G2 or the signal ratio R2/G2 exceeds the lower limit line 93 of the oxygen saturation of 0% or on the contrary becomes lower than the upper limit line 94 of the oxygen saturation of 100%. Here, the oxygen saturation calculation section 83 sets the oxygen saturation to 0% when the calculated oxygen saturation is lower than the lower limit line 93, and sets the oxygen saturation to 100% when the calculated oxygen saturation exceeds the upper limit line 94. In addition, when a point corresponding to the signal ratio B1/G2 and the signal ratio R2/G2 deviates from a region between the lower limit line 93 and the upper limit line 94, display showing that the reliability of the oxygen saturation in the pixel is low may be performed, or the oxygen saturation may not be calculated.

The image generation section 84 generates an oxygen saturation image by performing the imaging of the oxygen saturation using the oxygen saturation calculated by the oxygen saturation calculation section 83. Specifically, the image generation section 84 acquires a B2 image signal, a G2 image signal, and an R2 image signal, and multiplies these image signals by the gain corresponding to the oxygen saturation for each pixel. Then, RGB image data is generated using the B2 image signal, the G2 image signal, and the R2 image signal multiplied by the gain. For example, in a pixel where the corrected oxygen saturation is 60% or more, the image generation section 84 multiplies all of the B2 image signal, the G2 image signal, and the R2 image signal by the same gain "1". In contrast, in a pixel where the corrected oxygen saturation is less than 60%, the image generation section 84 multiplies the B2 image signal by the gain less than "1" and multiplies the G2 image signal and the R2 image signal by the gain of "1" or more. RGB image data generated using the B2 image signal, the G2 image signal, and the R2 image signal after the gain processing is the oxygen saturation image.

In the oxygen saturation image generated by the image generation section 84, a high oxygen region (region having an oxygen saturation of 60% to 100%) is expressed in the same color as the normal observation image. On the other hand, a low oxygen region where the oxygen saturation is less than a specific value (region having an oxygen saturation of 0% to 60%) is expressed in a different color (pseudo color) from the normal observation image.

Although the image generation section 84 performs gain multiplication for pseudo coloring only for the low oxygen region in the present embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

In addition, the diagnostic information calculation unit 65 includes a storage section 85, a pixel specification section 86, and a difference value calculation section 87.

The storage section 85 stores the oxygen saturation calculated by the oxygen saturation calculation section 83. In the present embodiment, the storage section 85 stores the data of the oxygen saturation corresponding to several (for example, about ten) past oxygen saturation images. Preferably, the storage section 85 stores the oxygen saturation data of at least one or more past oxygen saturation images. The past oxygen saturation stored in the storage section 85 is used by the pixel specification section 86 and the difference value calculation section 87.

In this specification, while an oxygen saturation image is generated in real time by imaging an observation target, the latest oxygen saturation image and the oxygen saturation used to generate the latest oxygen saturation image are referred to as a "current" oxygen saturation image and a "current" oxygen saturation, respectively. In this case, an oxygen saturation image generated before the current oxygen saturation image is referred to as a "past" oxygen saturation image, and the oxygen saturation used to generate the past oxygen saturation image is referred to as a "past" oxygen saturation.

The pixel specification section 86 acquires the current oxygen saturation from the oxygen saturation calculation section 83, compares the current oxygen saturation with a specific range set in advance for each pixel, and specifies the position of an out-of-range pixel having a value of the oxygen saturation deviating from the specific range in the current oxygen saturation image. In addition, the pixel specification section 86 specifies the position of an in-range pixel having a value of the oxygen saturation within the specific range by comparing the current oxygen saturation with the specific range for each pixel.

In addition, the pixel specification section 86 reads the past oxygen saturation from the storage section 85, compares the oxygen saturation with a specific range for each pixel, and specifies the position of an out-of-range pixel having a value of the oxygen saturation deviating from the specific range in the past oxygen saturation image and specifies the position of an in-range pixel having a value of the oxygen saturation within the specific range in the past oxygen saturation image. The specific range used for comparison with the past oxygen saturation is the same as the specific range used for comparison with the current oxygen saturation. In addition, when a plurality of past oxygen saturations are stored in the storage section 85, the specification of the out-of-range pixel and the in-range pixel in the past oxygen saturation image is performed for all or some of the plurality of past oxygen saturations (for at least one past oxygen saturation) according to the setting. In the present embodiment, the pixel specification section 86 specifies the out-of-range pixel and the in-range pixel for all of the past oxygen saturations stored in the storage section 85.

More specifically, the specific range is a range where the oxygen saturation is 60% or more (upper limit 100%), for example. In this case, in the current oxygen saturation image, the pixel specification section 86 specifies a low oxygen pixel (out-of-range pixel) in which the oxygen saturation is less than 60% (lower limit 0%), and specifies a high oxygen pixel (in-range pixel) in which the oxygen saturation is equal to or greater than 60%. Also for the past oxygen saturation, a low oxygen pixel (out-of-range pixel) and a high oxygen pixel (in-range pixel) are similarly specified. Needless to say, the specific range is arbitrary, and the values of upper and lower limits may be set to different values.

The difference value calculation section 87 includes a first average value calculation section 87A and a second average value calculation section 87B. The first average value calculation section 87A acquires the oxygen saturation of the current oxygen saturation image from the oxygen saturation calculation section 83, and acquires the position information of the out-of-range pixels of the current oxygen saturation image from the pixel specification section 86. Then, by using these, the average value (hereinafter, referred to as a first average value) of the oxygen saturation of the out-of-range pixels is calculated for the current oxygen saturation image. For example, the first average value is an average value of the oxygen saturation of the low oxygen pixels in the current oxygen saturation image.

On the other hand, the second average value calculation section 87B acquires the oxygen saturation of the current oxygen saturation image from the oxygen saturation calculation section 83, and acquires the oxygen saturation of the past oxygen saturation image from the storage section 86. In addition, the second average value calculation section 87B acquires the position information of the in-range pixels of the current oxygen saturation image and the position information of the in-range pixels of the past oxygen saturation image from the pixel specification section 86. Then, by using these, the average value (hereinafter, referred to as a second average value) of the oxygen saturation of the in-range pixels is calculated for each of the oxygen saturation images from the past to the present. For example, an average value of the oxygen saturation of the high oxygen pixels from the past to the present is calculated.

The difference value calculation section 87 calculates a difference value between the first and second average values (value obtained by subtracting the second average value from the first average value). Then, the calculated difference value is input to the image display signal generation unit 66 as diagnostic information. Accordingly, when displaying the oxygen saturation image on the monitor 18, the image display signal generation unit 66 further displays the difference value calculated by the difference value calculation section 87 on the monitor 18.

Figure 12:
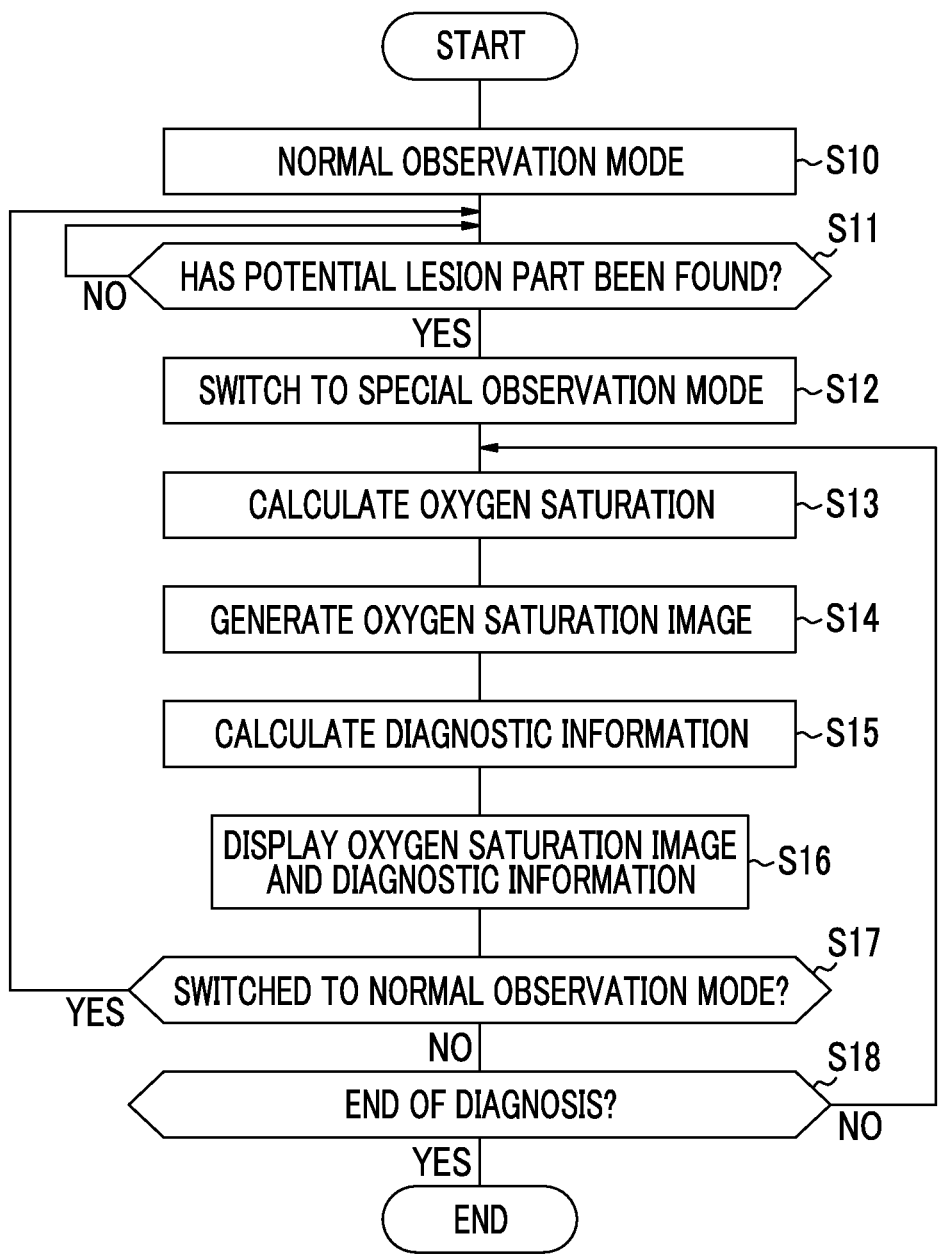
FIG. 12 is a flowchart showing the operation of the endoscope system.

Next, the flow of observation using the endoscope system 10 according to the present embodiment will be described with reference to the flowchart in FIG. 12. First, in the normal observation mode, screening is performed from the most distant view state (S10). In the normal observation mode, a normal observation image is displayed on the monitor 18. When a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, the potential lesion part is diagnosed.

In the special observation mode, the first and second white light beams are alternately emitted to the observation target in synchronization with the imaging frame of the sensor 48. Accordingly, the sensor 48 outputs the R1 image signal, the G1 image signal, and the B1 image signal in the first frame, and outputs the R2 image signal, the G2 image signal, and the B2 image signal in the second frame (imaging step). Then, in the processor device 16, when these imaging signals are received by the receiving unit 54 (receiving step), the signal ratio calculation section 81 calculates signal ratios B1/G2 and R2/G2, and the oxygen saturation calculation section 83 calculates the oxygen saturation for each pixel based on the signal ratios (S13: oxygen saturation calculating step). Then, the image generation section 84 generates an oxygen saturation image based on the image signals B2, G2, and R2 and the oxygen saturation calculated by the oxygen saturation calculation section 83 (S14: oxygen saturation image generation step).

On the other hand, when the oxygen saturation calculation section 83 calculates the oxygen saturation, the diagnostic information calculation unit 65 calculates a difference value as diagnostic information based on the oxygen saturation (S15: diagnostic information calculation step). Specifically, as shown in FIG. 13, the diagnostic information calculation step S15 includes: a pixel specifying step S151 in which the pixel specification section 86 specifies an out-of-range pixel and an in-range pixel for the current and past oxygen saturation images; a first average value calculation step S152 in which the first average value calculation section 87A calculates an average value (first average value) of the oxygen saturation of the out-of-range pixels for the current oxygen saturation image; a second average value calculation step S153 in which the second average value calculation section 87B calculates an average value (second average value) of the oxygen saturation of the oxygen saturation of the in-range pixels for the current and past oxygen saturation images; and a difference value calculation step S154 of calculating a difference value by subtracting the second average value from the first average value.

As shown in FIG. 14, an oxygen saturation image 161 and a difference value 162 (diagnostic information) that have been generated and calculated as described above are displayed on the monitor 18 (S16: display step). Since the oxygen saturation image 161 is pseudo-colored based on the current oxygen saturation, a low oxygen region 163 where the oxygen saturation is low is displayed bluish, for example. By this color, the lowness of the oxygen saturation is displayed. Therefore, when a skilled doctor looks at the colors of the low oxygen region 163 and other high oxygen regions 164 where the oxygen saturation is high, it is possible to determine whether or not the low oxygen region 163 is a lesion. However, since the value of the oxygen saturation changes with a subject, this determination is not always easy depending on a doctor.

Therefore, in the endoscope system 10, not only is the oxygen saturation of a potential lesion part displayed by the oxygen saturation image 161, but also the difference value 162 calculated using the oxygen saturation is displayed as diagnostic information together with the oxygen saturation image 161. As can be seen from this calculation method, the difference value 162 is a numerical value indicating the lowness of the oxygen saturation of the low oxygen region 163 objectively with the oxygen saturation of the high oxygen region 164 of the subject under examination as a reference. Therefore, by referring to the numerical value of the difference value, a doctor can easily determine whether or not the low oxygen region 163 displayed in the oxygen saturation image 161 is in hypoxia so as to be determined as a serious lesion in the subject under examination. For example, if the difference value 162 is small, the subject under examination is an individual including normal tissue having a greater tendency to be observed as having hypoxia compared with other subjects. In this case, even if the low oxygen region 163 is displayed in the oxygen saturation image 161, a possibility that the low oxygen region 163 will not be a serious lesion can be easily identified. On the other hand, if the difference value is large, it is clear that the low oxygen region 163 displayed in the oxygen saturation image 161 is in serious hypoxia for this subject. Accordingly, a serious lesion may be suspected.

In addition, these operations are repeatedly performed until switching to the normal observation mode (S17) or until the end of diagnosis (S18).

As described above, the endoscope system 10 calculates the oxygen saturation by imaging the observation target, and calculates the difference value 162 as diagnostic information using the oxygen saturation. Therefore, compared with a case where only the oxygen saturation image 161 (or the value of the oxygen saturation) is provided to a doctor, the endoscope system 10 can calculate objective diagnostic information, which is easier to understand than the oxygen saturation, and provide the objective diagnostic information to the doctor.

In the first embodiment, in order to calculate the difference value 162, current and past in-range pixels are specified, and the average value of the oxygen saturation is calculated as the second average value. However, it is also possible to calculate the average value of the oxygen saturation of the in-range pixels included in the current oxygen saturation and set this as the second average value. That is, the past oxygen saturation may not be used in order to calculate the second average value indicating the measure of the oxygen saturation of normal tissue. In this case, the storage section 85 is not necessary. However, when the second average value is calculated using only the current oxygen saturation, the second average value may change for every imaging of the observation target depending on the relative position or direction (angle) of the observation target and the distal portion 24, the movement of the observation target, or the like. Since the second average value is a value indicating the approximately universal oxygen saturation of normal tissue of the subject under examination, it is preferable that such error is as small possible. Therefore, as in the first embodiment, it is preferable to specify the current and past in-range pixels and use the average value of the oxygen saturation as the second average value. In this manner, at least the calculation error of the second average value can be suppressed. As a result, the accuracy of the difference value 162 as diagnostic information is improved.

In addition, since the second average value is a value indicating the approximately universal oxygen saturation of normal tissue of the subject under examination as described above, the oxygen saturation of the in-range pixel included in the current oxygen saturation may not be used in calculating the second average value. That is, an in-range pixel may be specified from the past oxygen saturation image without using the current oxygen saturation, and the average value of the oxygen saturation may be set as the second average value. In addition, when an accurate second average value is calculated using a plurality of past oxygen saturations, the second average value may be calculated only once and the same value may be continuously used thereafter. However, when the oxygen saturation image 161 and the difference value 162 are calculated and displayed in real time, the second average value may change from the past second average value depending on a situation. For this reason, it is preferable to calculate the second average value using the current oxygen saturation and the oxygen saturation for several past frames with respect to the current oxygen saturation. In this case, a possibility that the accurate difference value 162 can be calculated is also increased when the oxygen saturation image 161 and the difference value 162 are displayed in real time for the observation target that changes with time.

In the first embodiment described above, the pixel specification section 86 sets the specific range, which is compared with the oxygen saturation in order to specify the out-of-range pixel and the in-range pixel, as a range where the oxygen saturation is 60% or more. However, as long as the low oxygen region 163 that is likely to be a lesion and the high oxygen region 164 that is likely to be normal tissue can be easily distinguished, the method of setting the specific range is arbitrary. For example, it is also possible to specify the out-of-range pixel and the in-range pixel based on the statistical data of the oxygen saturation calculated by the oxygen saturation calculation section 83. Specifically, using the standard deviation σ, a pixel in which the oxygen saturation is within a range of, for example, ±3σ or ±6σ may be set as an in-range pixel, and a pixel in which the oxygen saturation deviates from the range may be set as an out-of-range pixel. In addition, since a pixel specified as an out-of-range pixel may have been incorrectly specified due to noise, when a pixel having a value of the oxygen saturation that is isolated is specified as an out-of-range pixel, the pixel is removed as noise (included in the in-range pixels). For example, by specifying several tens of pixels connected to each other as out-of-range pixels, it is possible to further improve the accuracy.

In addition, the pixel specification section 86 may calculate the gradient of the oxygen saturation so that a predetermined amount portion or more is extracted by the gradient. When a predetermined amount of portion or more extracted by the gradient forms a closed curve, pixels inside the closed curve may be specified as out-of-range pixels, and pixels outside the closed curve may be specified as in-range pixels. The gradient can be easily calculated by filtering using the Sobel operator or the like. Before performing determination regarding a closed curve, if the edge is supplemented using morphology or the like, the detection accuracy is further improved. A portion in which the line drawn by the edge is a circle may be extracted using the Hough transform.

In addition, the shape of the typical oxygen saturation distribution of lesions may be stored in advance in the pixel specification section 86 as a template, and a portion that matches the template may be specified as the out-of-range pixels, and the other portions may be specified as the in-range pixels. As the template, a typical template may be given. Alternatively, the template may be updated by machine learning.

[Second Embodiment]

Figure 15:
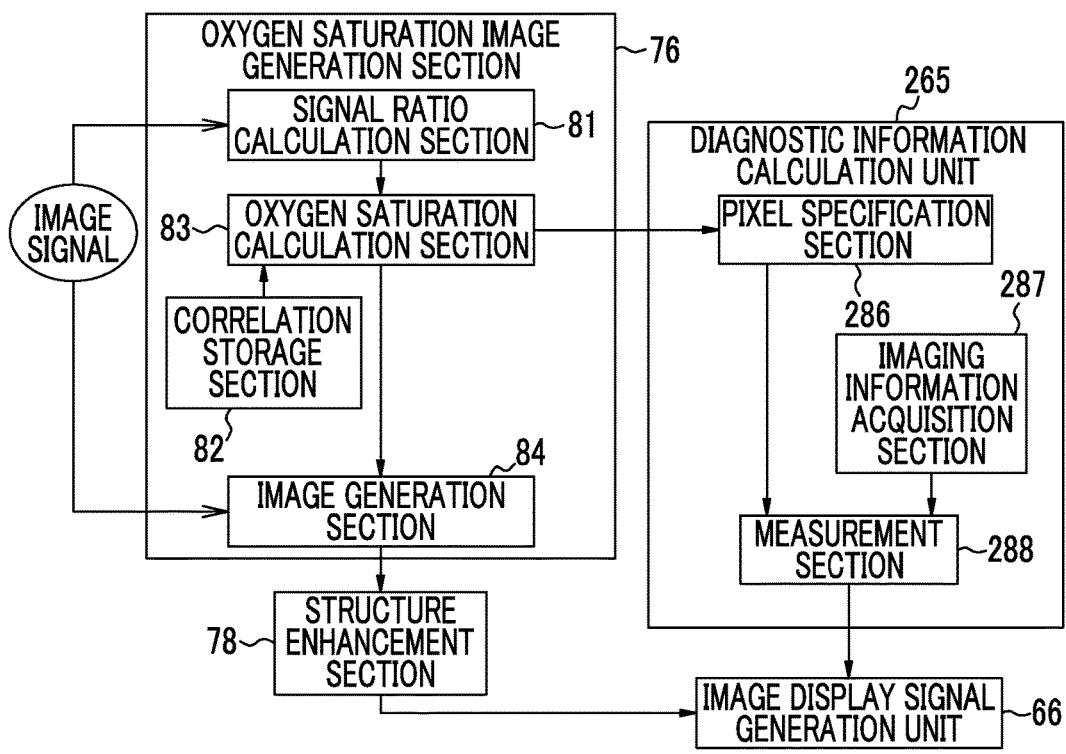
FIG. 15 is a block diagram showing an oxygen saturation image generation section and a diagnostic information calculation unit in a second embodiment.

An endoscope system of a second embodiment is formed by replacing the diagnostic information calculation unit 65 of the first embodiment with a diagnostic information calculation unit 265 shown in FIG. 15. Other configurations are the same as the endoscope system 10 according to the first embodiment.

The diagnostic information calculation unit 265 includes a pixel specification section 286, an imaging information acquisition section 287, and a measurement section 288. The pixel specification section 286 acquires the current oxygen saturation from the oxygen saturation calculation section 83, and specifies an out-of-range pixel and an in-range pixel. The method of specifying the out-of-range pixel and the in-range pixel is the same as that in the first embodiment. That is, the out-of-range pixel is a low oxygen pixel having a low oxygen saturation, and the in-range pixel is a high oxygen pixel having a high oxygen saturation.

The imaging information acquisition section 287 acquires information regarding the number of pixels, the pixel size, or the imaging distance of the sensor 48 by acquiring the ID indicating the type of the connected endoscope 12 or information regarding the driving state of a zoom lens from a CPU (not shown) of the processor device 16.

The measurement section 288 includes a look-up table (LUT) stored in advance in which the information of the out-of-range pixel specified by the pixel specification section 286 and the information regarding the number of pixels, the pixel size, or the imaging distance of the sensor 48 that is input from the imaging information acquisition section 287 correspond to the area. Using the input information and the LUT, the measurement section 288 measures the area of the range where out-of-range pixels are present. The area calculated by the measurement section 288 is output to the image display signal generation unit 66 as diagnostic information.

Figure 16:
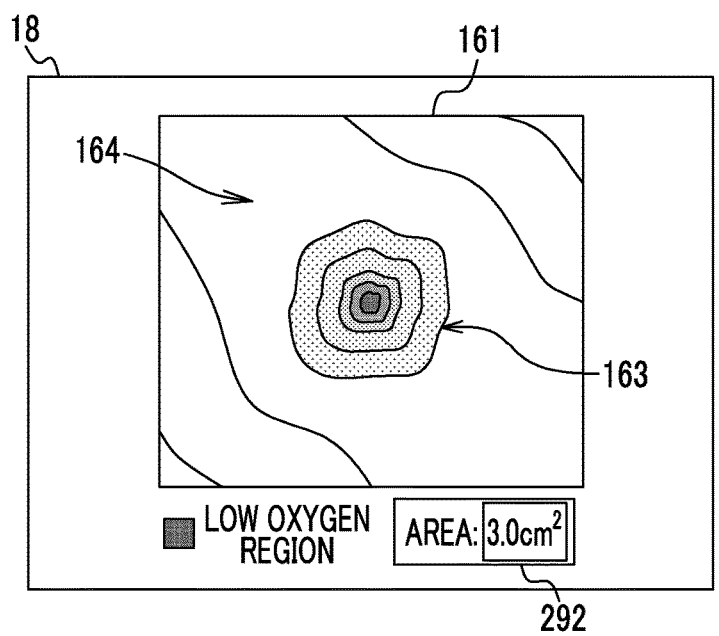
FIG. 16 is an explanatory diagram showing the operation in the second embodiment.

When the diagnostic information calculation unit 265 is formed as described above, as shown in FIG. 16, an oxygen saturation image 161 in which a low oxygen region 163 and a high oxygen region 164 are displayed by pseudo coloring and an area 292 of the low oxygen region 163 are displayed on the monitor 18. According to the oxygen saturation image 161, the area 292 of the low oxygen region 163 can be estimated, but this is not always easy. Therefore, calculating the area 292 of the low oxygen region 163, which is likely to be a lesion, specifically and displaying the calculated area 292 as in the present embodiment help in diagnosis.

In the second embodiment described above, the area 292 of the low oxygen region 163 is displayed based on the information of the specified out-of-range pixel or the like. However, instead of this, the length of the low oxygen region 163 in a specific direction, for example, the lengths of the oxygen saturation image 161 in the horizontal and vertical directions or the radius or diameter of a circular range including the low oxygen region 163 may be calculated and displayed as diagnostic information. That is, as long as the diagnostic information calculation unit 265 displays the information regarding the size of the low oxygen region 163 as diagnostic information, the specific content of the diagnostic information is arbitrary.

In addition, both of the information regarding the size of the low oxygen region 163 in the second embodiment and the difference value of the first embodiment may be calculated and displayed.

[Third Embodiment]

Figure 17:
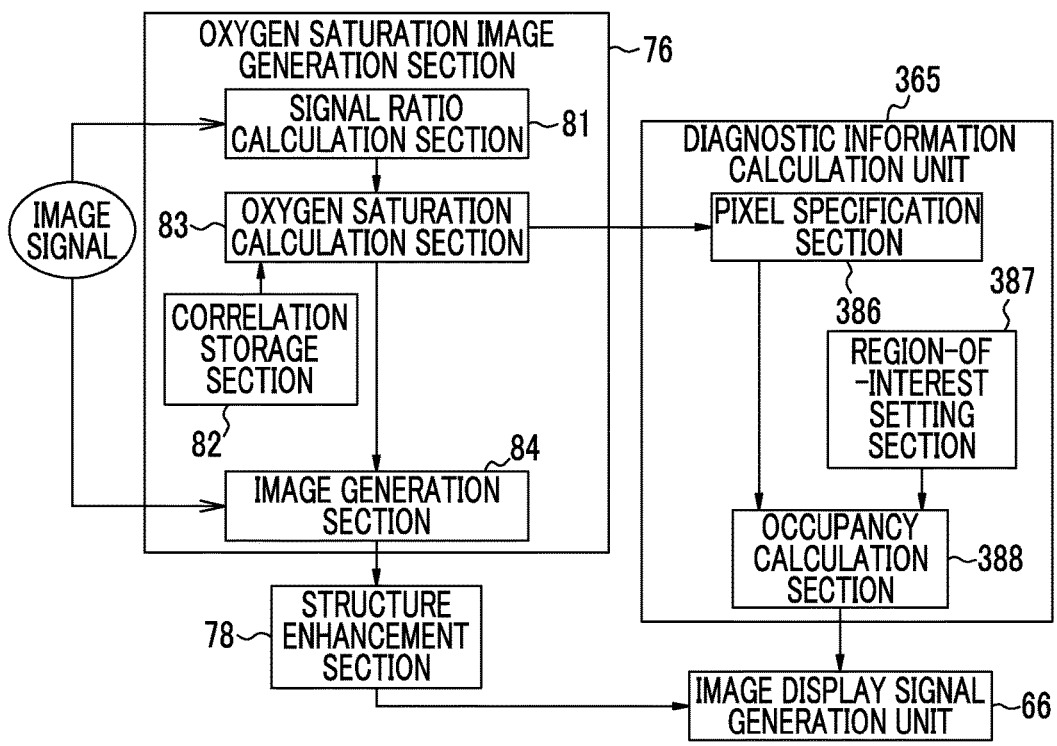
FIG. 17 is a block diagram showing an oxygen saturation image generation section and a diagnostic information calculation unit in a third embodiment.

An endoscope system of a third embodiment is formed by replacing the diagnostic information calculation unit 65 of the first embodiment with a diagnostic information calculation unit 365 shown in FIG. 17. Other configurations are the same as that of the endoscope system 10 according to the first embodiment.

The diagnostic information calculation unit 365 includes a pixel specification section 386, a region-of-interest setting section 387, and an occupancy calculation section 388. The pixel specification section 386 acquires the current oxygen saturation from the oxygen saturation calculation section 83, and specifies an out-of-range pixel and an in-range pixel. The method of specifying the out-of-range pixel and the in-range pixel is the same as that in the first embodiment. That is, the out-of-range pixel is a low oxygen pixel having a low oxygen saturation, and the in-range pixel is a high oxygen pixel having a high oxygen saturation.

The region-of-interest setting section 387 receives a setting input of a doctor using the console 20, and sets a region of interest that is used by the occupancy calculation section 388. The region of interest is set with reference to the oxygen saturation image 161 displayed on the monitor 18, for example.

The occupancy calculation section 388 calculates the proportion (hereinafter, referred to as an occupancy) of out-of-range pixels in the region of interest as diagnostic information. The occupancy is a numerical value that indicates the ratio of the number of out-of-range pixels in the set region of interest to the number of pixels in the set region of interest as a percentage. The occupancy calculation section 388 outputs the calculated occupancy to the image display signal generation unit 66.

Figure 18:
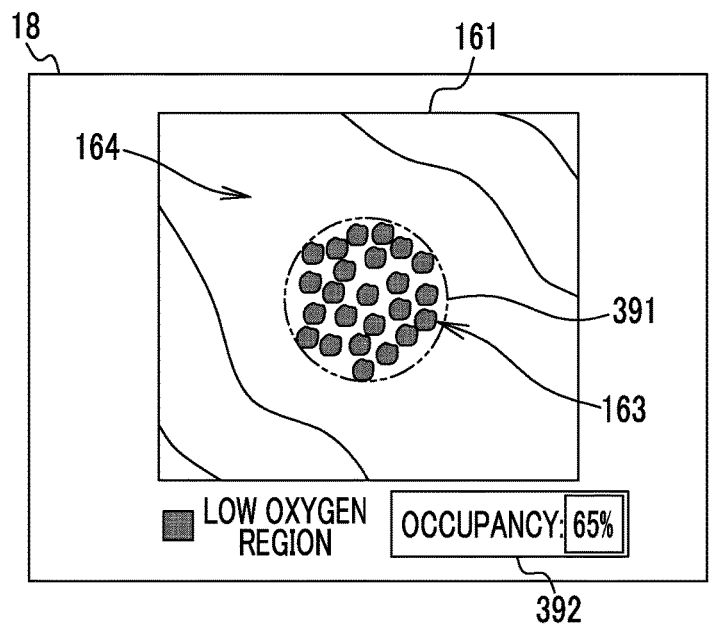
FIG. 18 is an explanatory diagram showing the operation in the third embodiment.

Therefore, as shown in FIG. 18, an oxygen saturation image 161 in which a low oxygen region 163 and a high oxygen region 164 are displayed by pseudo coloring, a set region of interest 391, and occupancy 392 of the low oxygen region 163 are displayed on the monitor 18. The approximate value of the occupancy 392 can be grasped by observing the oxygen saturation image 161. However, it is difficult to grasp a value that is specific and objective. In particular, in the case of cancer that is dyed in a spot pattern form when a potential lesion part, which forms the spot-pattern-like low oxygen region 163 as shown in FIG. 18, is dyed with iodine or the like, the density of the spot pattern becomes a measure of diagnosis. Accordingly, displaying the occupancy 392 as diagnostic information helps in diagnosis of such cancer.

In addition, although a region of a part of the oxygen saturation image 161 is set as the region of interest 391 by the doctor in the third embodiment described above, the entire oxygen saturation image 161 may be set as the region of interest 391. In addition, the region-of-interest setting section 387 may set the region of interest 391 automatically by detecting a range including the specified out-of-range pixel. In these cases, the setting of the region of interest 391 by the doctor is not necessary.

In addition, although the region of interest 391 is set as a circular region, the shape of the region of interest 391 is arbitrary. For example, the region of interest 391 may be set as a rectangle.

The calculation and display of the occupancy 392 in the third embodiment can be combined with the first and second embodiments. That is, the difference value 162 and the occupancy 392 may be calculated and displayed, and the size of the low oxygen region 163, such as the area, and the occupancy 392 may be calculated and displayed. In addition, all of the difference value 162, the size of the low oxygen region 163, such as the area, and the occupancy 392 may be calculated and displayed.

In the third embodiment described above, the occupancy 392 is calculated and displayed as diagnostic information. However, instead of the occupancy 392, in the region of interest 391, a statistic regarding the distribution of out-of-range pixels, such as a variance, may be calculated and displayed as diagnostic information. In this case, it is preferable that the occupancy calculation section 388 be a statistic calculation section that calculates the statistic described above. Needless to say, the occupancy calculation section 388 may serve as a statistic calculation section, so that both of the occupancy and the statistic are calculated and displayed. Thus, also when the statistic, such as a variance, is calculated and displayed as diagnostic information, the difference value 162 or the size in the first and second embodiments can be calculated and displayed together therewith.

[Fourth Embodiment]

Figure 19:
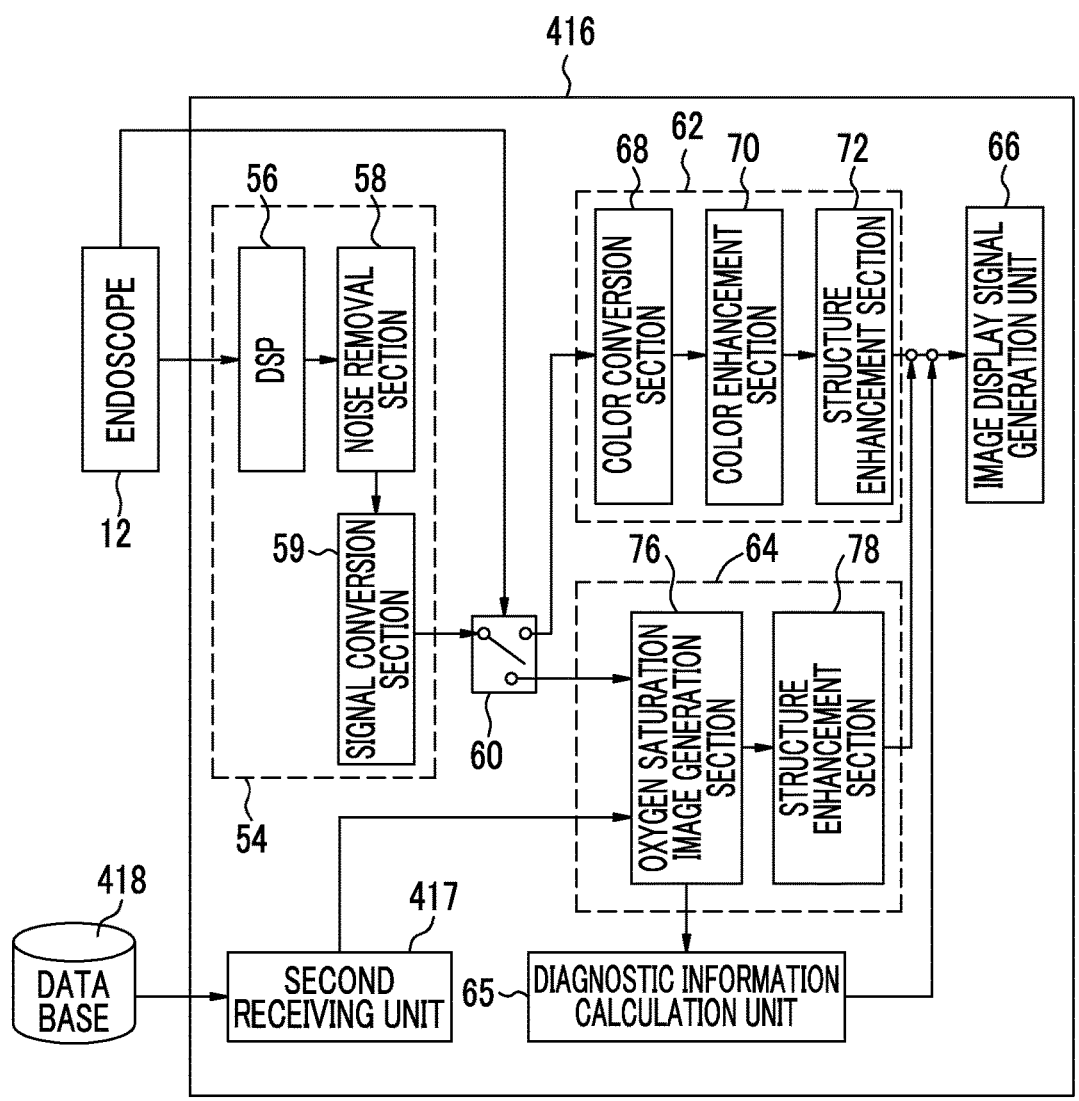
FIG. 19 is a block diagram showing a processor device according to a fourth embodiment.

As shown in FIG. 19, a processor device 416 according to a fourth embodiment includes a second receiving unit 417 in addition to the processor device 16 according to the first embodiment. Other configurations are the same as that of the endoscope system 10 according to the first embodiment.

The second receiving unit 417 is connected to a database 418, and is an interface for receiving oxygen saturation images captured in the past or videos, various image signals used for the generation of oxygen saturation images, and the like (hereinafter, referred to as past data) from the database 418. The second receiving unit 417 inputs the received past data to the oxygen saturation image generation section 76.

Accordingly, the oxygen saturation image generation section 76 acquires the oxygen saturation at an arbitrary point in time in the past and the oxygen saturation before the arbitrary point from past data. In this case, the "oxygen saturation at an arbitrary point in time in the past" corresponds to the current oxygen saturation in the first embodiment, and the "oxygen saturation before the arbitrary point" corresponds to the oxygen saturation in the past in the first embodiment. Therefore, although the processor device 16 according to the first embodiment calculates and generates the oxygen saturation and the diagnostic information based on the image signal obtained by imaging the observation target in real time, the processor device 416 according to the fourth embodiment can calculate and display diagnostic information similarly for the past data.

In addition, the database 418 may be built into the processor device 416, or may be connected to the processor device 416 through a hospital network or the like.

[Fifth Embodiment]

Figure 20:
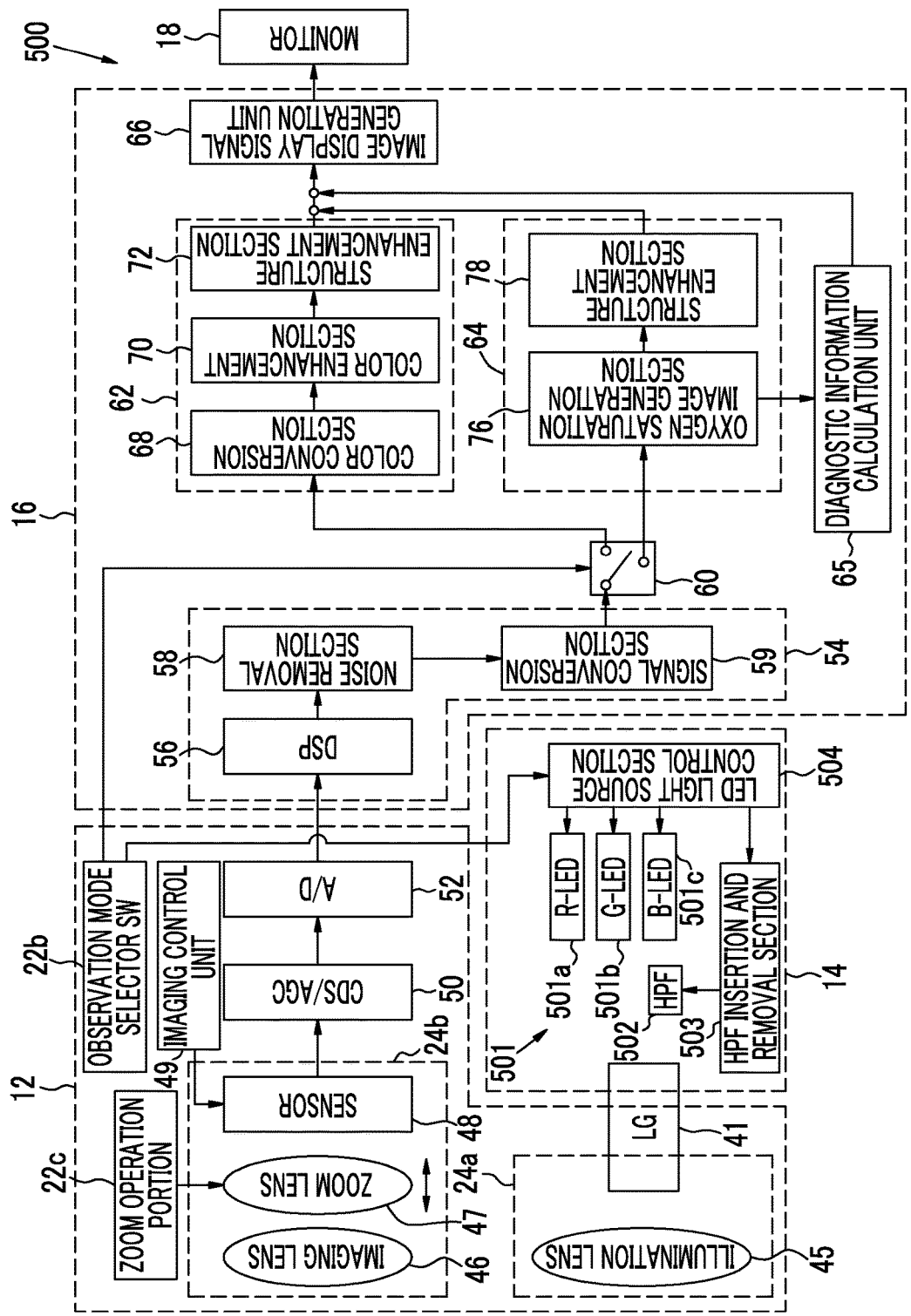
FIG. 20 is a block diagram of an endoscope system according to a fifth embodiment.

As shown in FIG. 20, in a light source device 14 of an endoscope system 700, a light emitting diode (LED) light source unit 501 and an LED light source control section 504 are provided instead of the first and second blue laser light sources 34 and 36 and the light source control unit 40. In addition, the phosphor 44 is not provided in an illumination optical system 24a of an endoscope system 500. Other than these, the endoscope system 500 is the same as the endoscope system 10 according to the first embodiment.

Figure 21:
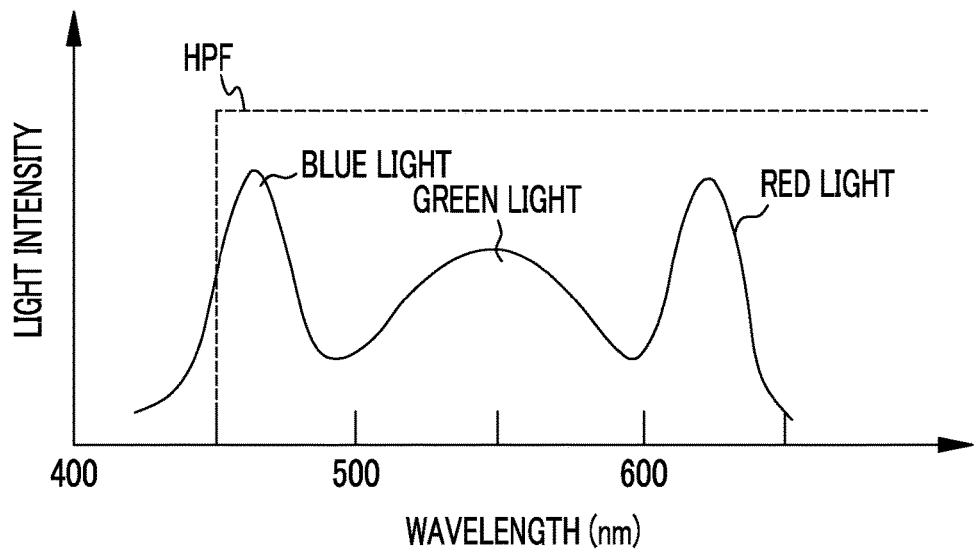
FIG. 21 is a graph showing the light emission band of an LED and the characteristics of an HPF.

The LED light source unit 501 includes an R-LED 501a, a G-LED 501b, and a B-LED 501c as light sources for emitting light limited to a specific wavelength band. As shown in FIG. 21, the R-LED 501a emits red band light (hereinafter, simply referred to as red light) having a wavelength of about 600 nm to 650 nm, for example. The center wavelength of the red light is about 620 nm to 630 nm. The G-LED 501b emits green band light (hereinafter, simply referred to as green light) having a wavelength of about 500 nm to 600 nm that is expressed by a normal distribution. The B-LED 501c emits blue band light (hereinafter, simply referred to as blue light) having a center wavelength of 445 nm to 460 nm.

In addition, the LED light source unit 501 includes a high pass filter (HPF) 502 that is removably inserted on the optical path of the blue light emitted from the B-LED 501c. The high pass filter 502 cuts the blue light having a wavelength in a wavelength band of about 450 nm or less, and allows light having a wavelength in a wavelength band higher than about 450 nm to be transmitted therethrough.

The cutoff wavelength (about 450 nm) of the high pass filter 502 is a wavelength at which the light absorption coefficient of oxygenated hemoglobin and the light absorption coefficient of reduced hemoglobin are almost equal (refer to FIG. 10), and the light absorption coefficient of oxygenated hemoglobin and the light absorption coefficient of reduced hemoglobin are reversed in the order of magnitude with the cutoff wavelength as a boundary. In the present embodiment, the correlation stored in the correlation storage section 82 is that the light absorption coefficient of oxygenated hemoglobin is larger than the light absorption coefficient of reduced hemoglobin. Accordingly, a signal based on the wavelength band equal to or lower than the cutoff wavelength is a cause by which incorrect oxygen saturation is calculated. Therefore, by preventing light having a wavelength in a wavelength band equal to or lower than the cutoff wavelength from being emitted to the observation target using the high pass filter 502 when acquiring at least the B1 image signal for calculating the oxygen saturation, the calculation accuracy of the oxygen saturation is improved.

Accordingly, the high pass filter 502 is inserted at the insertion position before the B-LED 501c in the special observation mode, and is retracted to the retraction position in the normal observation mode. The insertion and removal of the high pass filter 502 is performed by an HPF insertion and removal section 503 under the control of the LED light source control section 504.

Figure 22:
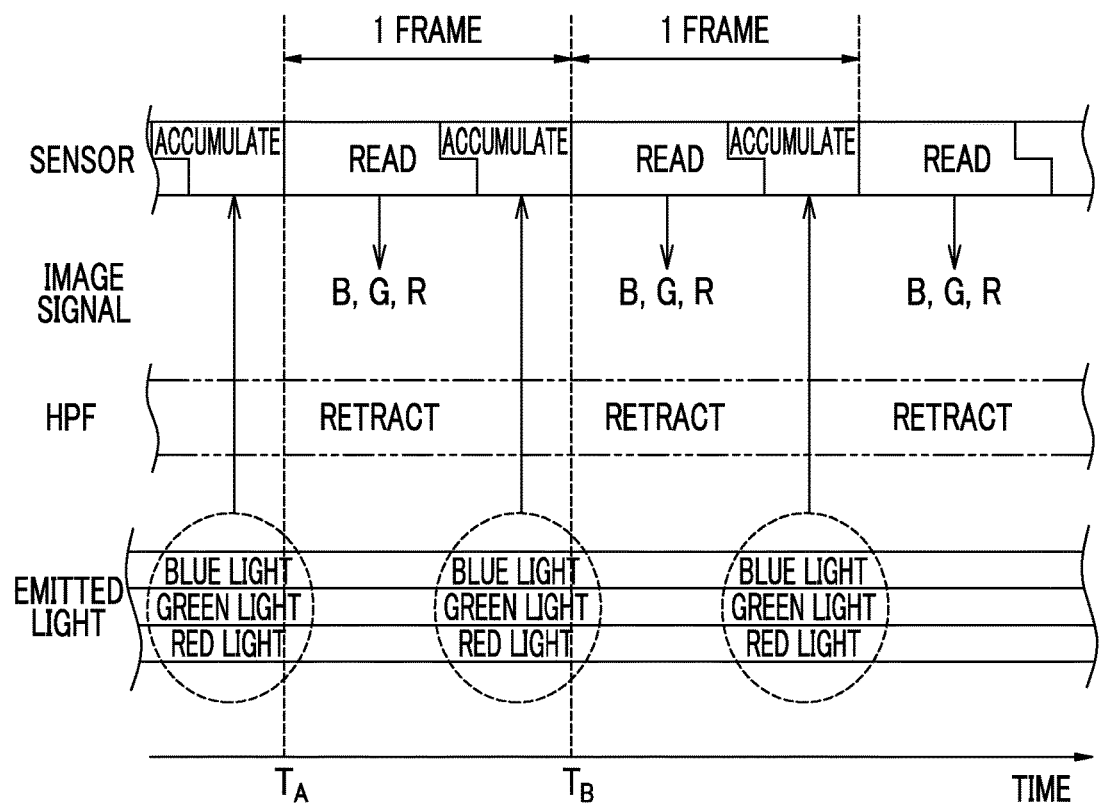
FIG. 22 is an explanatory diagram showing imaging control in the normal observation mode in the fifth embodiment.

The LED light source control section 504 controls ON/OFF of the LEDs 501a to 501c of the LED light source unit 501 and the insertion and removal of the high pass filter 502. Specifically, as shown in FIG. 22, in the normal observation mode, the LED light source control section 504 turns on all of the LEDs 501a to 501c and retracts the high pass filter 502 from the optical path of the B-LED 501c. Accordingly, white light in which blue light, green light, and red light are superimposed are emitted to the observation target, and the sensor 48 images the observation target with reflected light of the white light and outputs an image signal of each color of B, G, and R.

Figure 23:
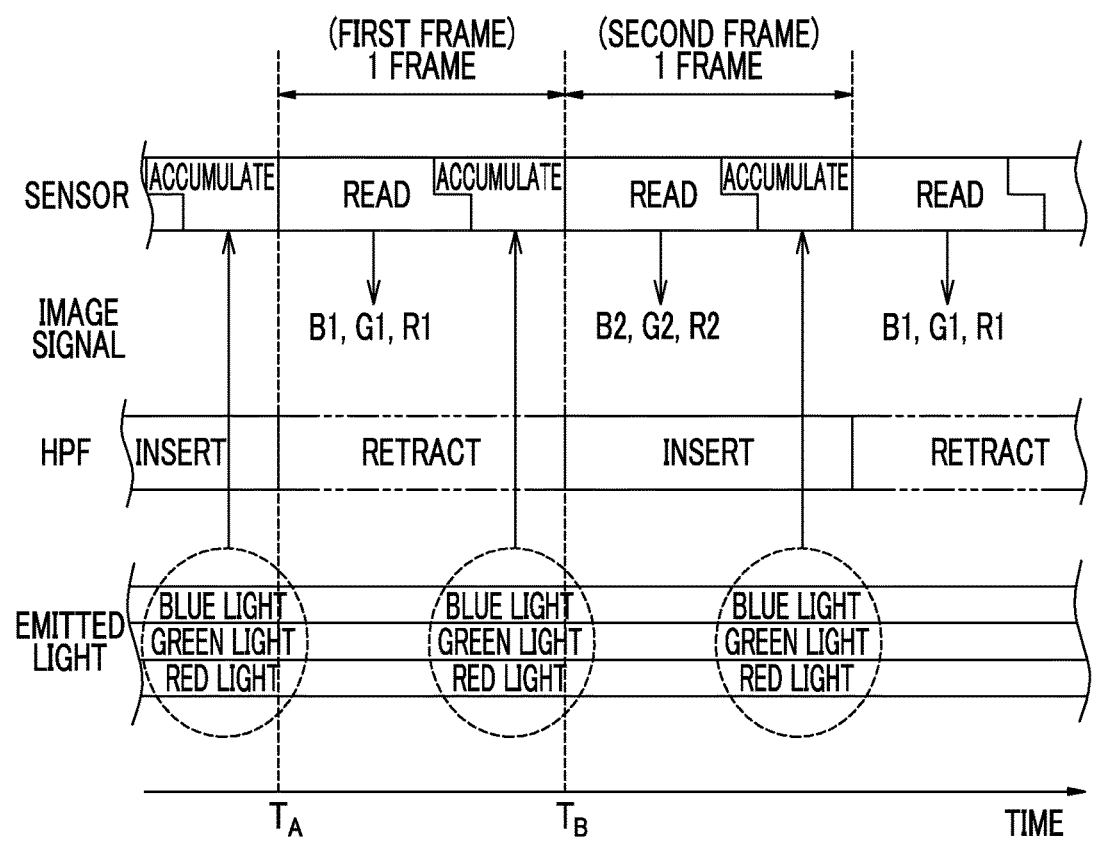
FIG. 23 is an explanatory view showing imaging control in the special observation mode in the fifth embodiment.

On the other hand, as shown in FIG. 23, in the special observation mode, the LED light source control section 504 inserts or retracts the high pass filter 502 for each frame in a state where all of the LEDs 501a to 501c are turned on. Accordingly, first mixed color light of blue light, green light, and red light when light having a wavelength in a wavelength band of 450 nm or less is cut off and second mixed color light of blue light, green light, and red light when light having a wavelength in a wavelength band of 450 nm or less is not cut off are alternately emitted to the observation target. The first mixed color light corresponds to the first white light in the first embodiment, and the second mixed color light corresponds to the second white light in the first embodiment.

Then, in the imaging control unit 49, a signal charge obtained by imaging the observation target under the first mixed color light is read in a reading period of the first frame, and the B1 image signal, the G1 image signal, and the R1 image signal are output. In addition, a signal charge obtained by imaging the observation target under the second mixed color light is read in a reading period of the second frame, and the B2 image signal, the G2 image signal, and the R2 image signal are output. Subsequent processing can be performed in the same manner as in the endoscope system 10.

In addition, the first and second mixed color light beams are first and second illumination light beams having different emission spectrums, and the R-LED 501a, the G-LED 501b, the B-LED 501c, and the high pass filter 502 form a light source that emits the first and second illumination light beams having different emission spectrums to the observation target.

[Sixth Embodiment]

Figure 24:
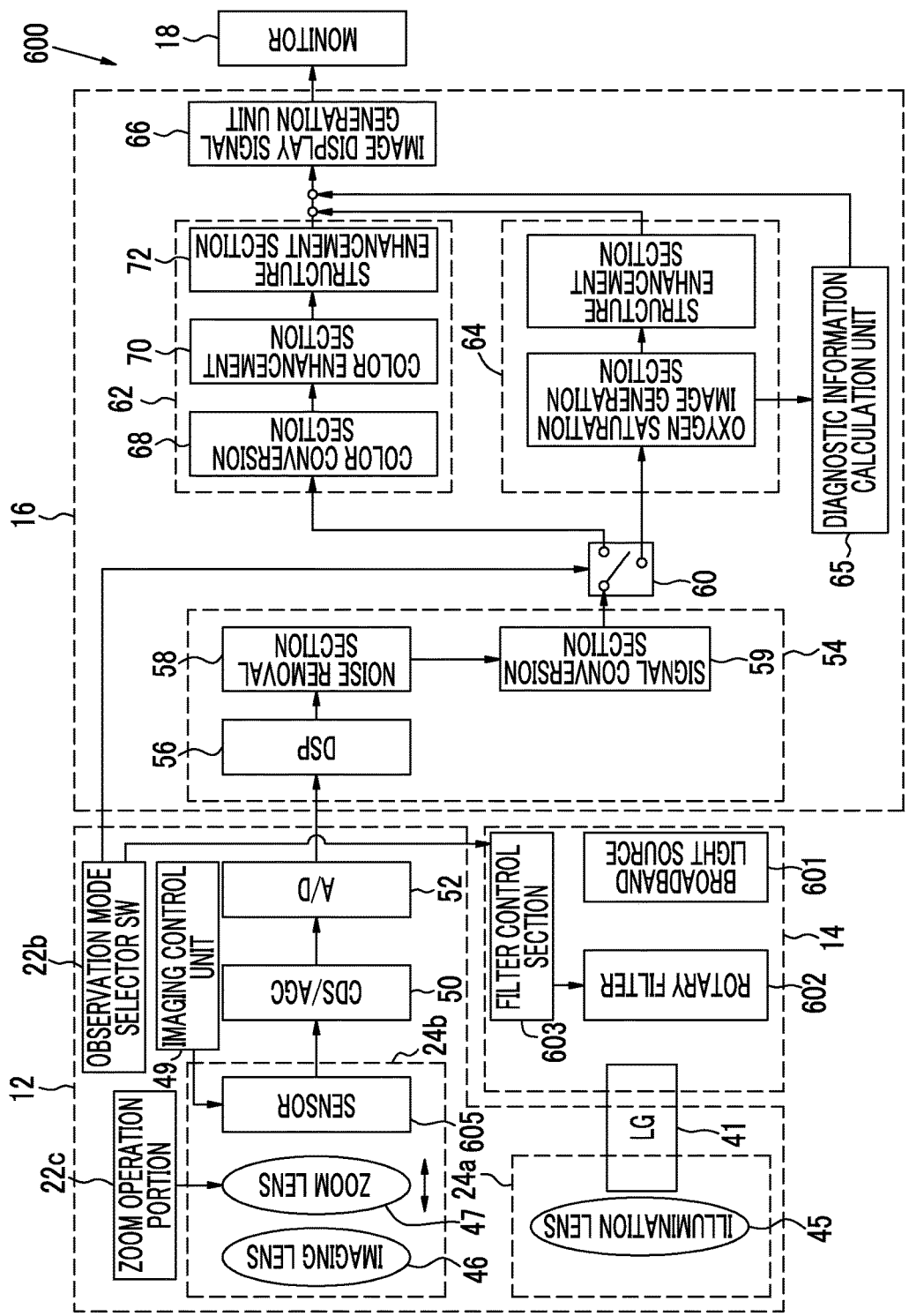
FIG. 24 is a block diagram of an endoscope system according to a sixth embodiment.

As shown in FIG. 24, in a light source device 14 of an endoscope system 600, a broadband light source 601, a rotary filter 602, and a rotary filter control section 603 are provided instead of the first and second blue laser light sources 34 and 36 and the light source control unit 40. A sensor 605 of the endoscope system 600 is a monochrome imaging device in which no color filter is provided. Therefore, the DSP 56 does not perform processing specific to the color imaging device, such as demosaic processing. Other than these, the endoscope system 600 is the same as the endoscope system 10 according to the first embodiment.

The broadband light source 601 is, for example, a xenon lamp or a white LED, and emits white light having a wavelength in a wavelength band ranging from blue to red. The rotary filter 602 includes a normal observation mode filter 610 and a special observation mode filter 611 (refer to FIG. 25), and can move in a radial direction between a first position for normal observation mode to place a normal observation mode filter 610 on the optical path, in which the white light emitted from the broadband light source 601 is incident on the light guide 41, and a second position for special observation mode to place a special observation mode filter 611 on the optical path. The movement of the rotary filter 602 to the first and second positions is controlled by the rotary filter control section 603 according to the selected observation mode. In addition, the rotary filter 602 rotates according to the imaging frame of the sensor 605 while being placed at the first or second position. The rotation speed of the rotary filter 602 is controlled by the rotary filter control section 603 according to the selected observation mode.

Figure 25:
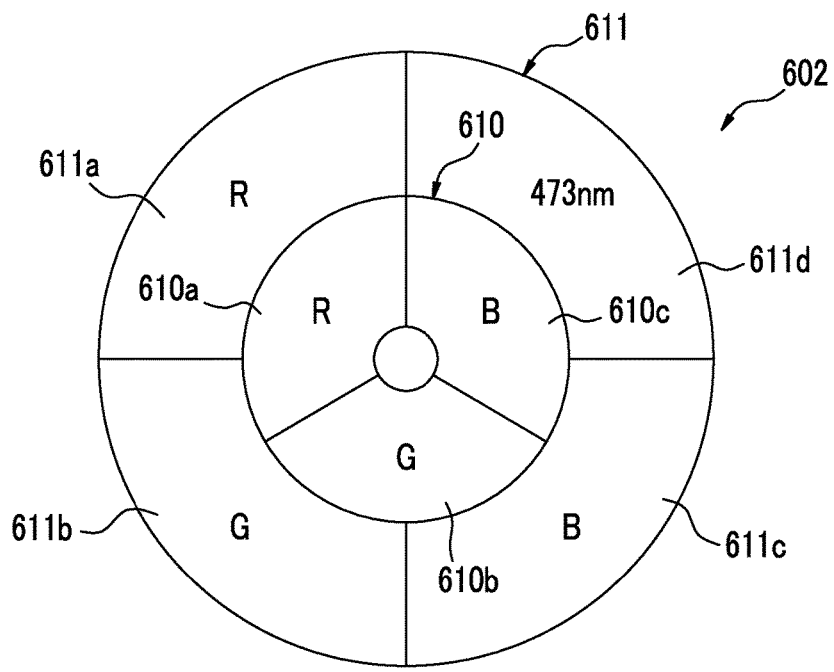
FIG. 25 is a plan view of a rotary filter.

As shown in FIG. 25, the normal observation mode filter 610 is provided in the inner peripheral portion of the rotary filter 602. The normal observation mode filter 610 includes an R filter 610a that transmits red light, a G filter 610b that transmits green light, and a B filter 610c that transmits blue light. Therefore, when the rotary filter 602 is placed at the first position for normal light observation mode, the white light from the broadband light source 601 is incident on one of the R filter 610a, the G filter 610b, and the B filter 610c according to the rotation of the rotary filter 602. As a result, red light, green light, and blue light are sequentially emitted to the observation target according to the transmitted filter, and the sensor 605 outputs sequentially an R image signal, a G image signal, and a B image signal by imaging the observation target with reflected light of the red light, the green light, and the blue light.

The special observation mode filter 611 is provided in the outer peripheral portion of the rotary filter 602. The special observation mode filter 611 includes an R filter 611a that transmits red light, a G filter 611b that transmits green light, a B filter 611c that transmits blue light, and a narrowband filter 611d that transmits narrowband light of 473±10 nm. Therefore, when the rotary filter 602 is placed at the second position for normal light observation mode, the white light from the broadband light source 601 is incident on one of the R filter 611a, the G filter 611b, the B filter 611c, and the narrowband filter 611d according to the rotation of the rotary filter 602. As a result, red light, green light, blue light, and narrowband light (473 nm) are sequentially emitted to the observation target according to the transmitted filter, and the sensor 605 outputs sequentially an R image signal, a G image signal, a B image signal, and a narrowband image signal by imaging the observation target with reflected light of the red light, the green light, the blue light, and the narrowband light.

The R image signal and the G image signal acquired in the special observation mode correspond to the R1 (or R2) image signal and the G1 (or G2) image signal in the first embodiment. In addition, the B image signal acquired in the special observation mode corresponds to the B2 image signal in the first embodiment, and the narrowband image signal corresponds to the B1 image signal. Accordingly, subsequent processing can be performed in the same manner as in the endoscope system 10 according to the first embodiment.

In addition, the broadband light source 601 and the rotary filter 602 form a light source that emits the first and second illumination light beams having different emission spectrums. In the present embodiment, a series of light emitted to the observation target by using the special observation mode filter 611 is the first illumination light, and a series of light emitted to the observation target by using the normal observation mode filter 610 is the second illumination light.

Although the oxygen saturation is calculated based on the signal ratio B1/G2 and the signal ratio R2/G2 in the first to sixth embodiments, it is also possible to calculate the oxygen saturation based on only the signal ratio B1/G2. In this case, it is preferable to store the correlation between the signal ratio B1/G2 and the oxygen saturation in the correlation storage section 82.

Although the oxygen saturation image obtained by imaging the oxygen saturation is generated and displayed in the first to sixth embodiments, a blood volume image obtained by imaging the blood volume may be generated and displayed in addition to the generation and display of the oxygen saturation image. Since the blood volume is correlated with the signal ratio R2/G2, a blood volume image obtained by imaging the blood volume can be generated by assigning different colors according to the signal ratio R2/G2.

In the first to sixth embodiments, the oxygen saturation is calculated. However, instead of or in addition to the oxygen saturation, other biological function information, such as an oxygenated hemoglobin index that is calculated from "blood volume×oxygen saturation (%)" or a reduced hemoglobin index that is calculated from "blood volume×(1−oxygen saturation) (%)", may be calculated.

Figure 26:
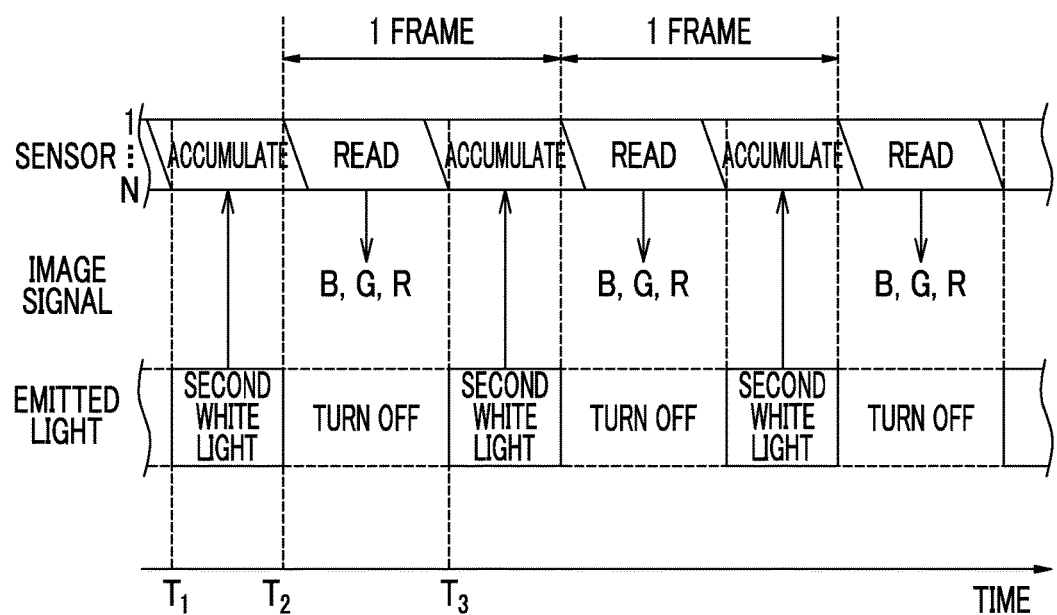
FIG. 26 is an explanatory view showing imaging control in the normal observation mode in the case of using a CMOS image sensor.
Figure 27:
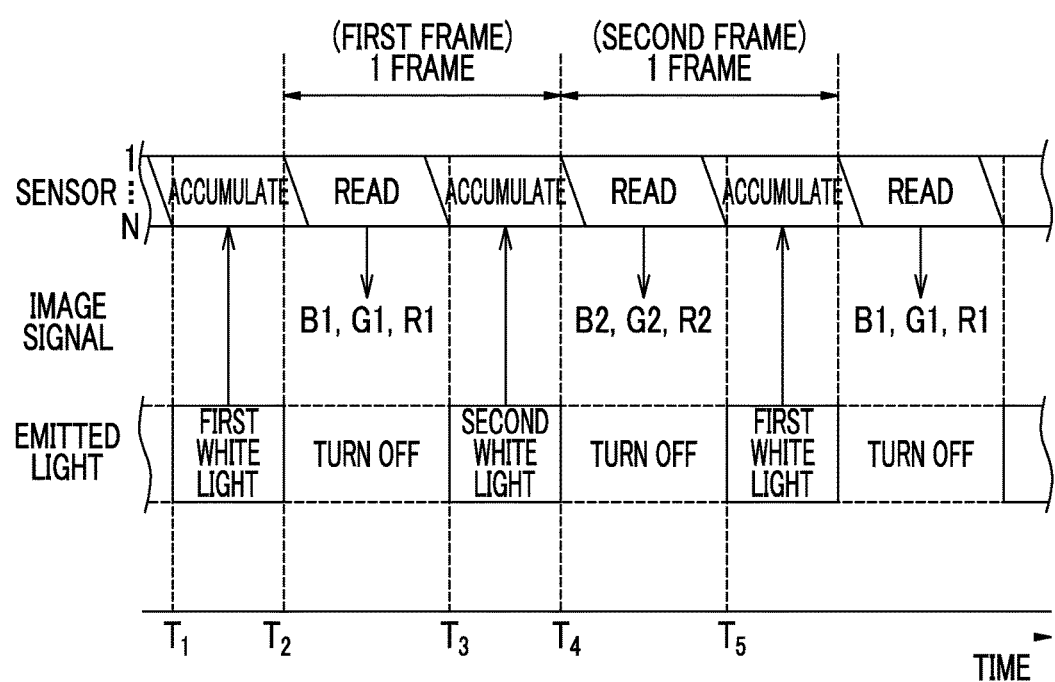
FIG. 27 is an explanatory view showing imaging control in the special observation mode in the case of using a CMOS image sensor.

Although the CCD image sensor is used as the sensor 48 in the first to sixth embodiments, a CMOS image sensor may also be used as the sensor 48. However, the CMOS image sensor is driven in a so-called rolling shutter method, and accumulation and reading of the signal charge are sequentially performed for each row (each of first to N-th rows) of pixels. For this reason, the timing of the accumulation and reading of the signal charge of each row differs according to each row. Therefore, switching between the first white light and the second white light is preferably performed in accordance with the reading timing. For example, as shown in FIG. 26, in the normal observation mode, the emission of the second white light is performed until the accumulation of the first row is completed (time T2) from the start of the accumulation of the N-th row (time T1), while the emission of the second white light is stopped until the reading of the N-th row is completed from the start of the reading of the first row. In addition, as shown in FIG. 27, in the special observation mode, the emission of the second white light is performed until the accumulation of the first row is completed (time T2) from the start of the accumulation of the N-th row (time T1), while the emission of the second white light is stopped until the reading of the N-th row is completed (time T3) from the start of the reading of the first row (time T2). Then, in the next frame, the emission of the first white light is performed until the accumulation of the first row is completed (time T4) from the start of the accumulation of the N-th row (time T3), while the emission of the first white light is stopped until the reading of the N-th row is completed (time T5) from the start of the reading of the first row (time T4). Thus, it is possible to standardize the length (exposure) of the substantial charge accumulation period of each row and to prevent the signal based on the first white light and the signal based on the second white light from being mixed. Therefore, even when a CMOS image sensor is used as the sensor 48, it is possible to accurately calculate the oxygen saturation as in the embodiments described above. The same is true for a case when the LED light source unit 501 or the broadband light source 601 and the rotary filter 602 are used instead of the first and second blue laser light sources 34 and 36.

What is claimed is:

1. An endoscope system processor device, comprising:
a receiving unit that receives an image signal obtained by imaging an observation target with an endoscope;
an oxygen saturation calculation unit that calculates an oxygen saturation based on the image signal;
a pixel specification unit that specifies an out-of-range pixel in which the oxygen saturation deviates from a specific range set in advance; and
a diagnostic information calculation unit that calculates diagnostic information as a numerical value using information of the out-of-range pixel,
wherein the pixel specification unit specifies an in-range pixel in which the oxygen saturation is within the specific range, and
the diagnostic information calculation unit includes a difference value calculation section that calculates a difference value between the oxygen saturation of the out-of-range pixel and the oxygen saturation of the in-range pixel.

2. The endoscope system processor device according to claim 1,
wherein the difference value calculation section includes a first average value calculation section that calculates an average value of the oxygen saturation of the out-of-range pixels and a second average value calculation section that calculates an average value of the oxygen saturation of the in-range pixels, and calculates a difference value between a first average value calculated by the first average value calculation section and a second average value calculated by the second average value calculation section.

3. The endoscope system processor device according to claim 2,
wherein the first average value calculation section calculates the first average value using one of the oxygen saturations, and
the second average value calculation section calculates the second average value using a plurality of the oxygen saturations.

4. The endoscope system processor device according to claim 3,
wherein the first average value calculation section calculates the first average value using the oxygen saturations that are current oxygen saturations, and
the second average value calculation section calculates the second average value using the oxygen saturations that are current and past oxygen saturations.

5. The endoscope system processor device according to claim 3,
wherein the first average value calculation section calculates the first average value using one specific oxygen saturation of the plurality of oxygen saturations that are past oxygen saturations, and
the second average value calculation section calculates the second average value using the plurality of past oxygen saturations.

6. The endoscope system processor device according to claim 1,
wherein the diagnostic information calculation unit includes a measurement section that measures a size of a region formed by the out-of-range pixels.

7. The endoscope system processor device according to claim 2,
wherein the diagnostic information calculation unit includes a measurement section that measures a size of a region formed by the out-of-range pixels.

8. The endoscope system processor device according to claim 3,
wherein the diagnostic information calculation unit includes a measurement section that measures a size of a region formed by the out-of-range pixels.

9. The endoscope system processor device according to claim 1,
wherein the diagnostic information calculation unit includes an occupancy calculation section that calculates an occupancy indicating a proportion of the out-of-range pixels in a set region of interest.

10. The endoscope system processor device according to claim 2,
wherein the diagnostic information calculation unit includes an occupancy calculation section that calculates an occupancy indicating a proportion of the out-of-range pixels in a set region of interest.

11. The endoscope system processor device according to claim 3,
    wherein the diagnostic information calculation unit includes an occupancy calculation section that calculates an occupancy indicating a proportion of the out-of-range pixels in a set region of interest.

12. The endoscope system processor device according to claim 1,
    wherein the diagnostic information calculation unit includes a statistic calculation section that calculates a statistic regarding distribution of the out-of-range pixels in the set region of interest.

13. The endoscope system processor device according to claim 2,
    wherein the diagnostic information calculation unit includes a statistic calculation section that calculates a statistic regarding distribution of the out-of-range pixels in the set region of interest.

14. An endoscope system using the endoscope system processor device according to claim 1, further comprising:
    A light source that emits light for irradiating the observation target;
    An imaging device that images the observation target and outputs the image signal.

15. An operation method for the endoscope system processor device according to claim 1, comprising:
    a receiving step in which the receiving unit receives an image signal obtained by imaging an observation target with an endoscope;
    an oxygen saturation calculation step in which the oxygen saturation calculation unit calculates an oxygen saturation based on the image signal;
    a pixel specification step in which the pixel specification unit specifies an out-of-range pixel in which the oxygen saturation deviates from a specific range set in advance; and
    a diagnostic information calculation step in which the diagnostic information calculation unit calculates diagnostic information as a numerical value using information of the out-of-range pixel.

* * * * *